(12) United States Patent
Stockley et al.

(10) Patent No.: US 11,414,402 B2
(45) Date of Patent: Aug. 16, 2022

(54) SULFONAMIDE-SUBSTITUTED CYANOPYRROLIDINES WITH ACTIVITY AS DUB INHIBITORS

(71) Applicant: MISSION THERAPEUTICS LIMITED, Cambridge (GB)

(72) Inventors: Martin Lee Stockley, Cambridge (GB); Mark Ian Kemp, Cambridge (GB); Andrew Madin, Cambridge (GB); Michael David Woodrow, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 20 days.

(21) Appl. No.: 16/615,040

(22) PCT Filed: May 30, 2018

(86) PCT No.: PCT/GB2018/051454
§ 371 (c)(1),
(2) Date: Nov. 19, 2019

(87) PCT Pub. No.: WO2018/220355
PCT Pub. Date: Dec. 6, 2018

(65) Prior Publication Data
US 2020/0172518 A1    Jun. 4, 2020

(30) Foreign Application Priority Data
May 31, 2017 (GB) ..................................... 1708652

(51) Int. Cl.
| | | |
|---|---|---|
| C07D 487/04 | (2006.01) | |
| C07D 403/12 | (2006.01) | |
| C07D 207/14 | (2006.01) | |
| C07D 401/12 | (2006.01) | |
| C07D 401/14 | (2006.01) | |
| C07D 403/14 | (2006.01) | |
| C07D 498/04 | (2006.01) | |

(52) U.S. Cl.
CPC ......... *C07D 403/12* (2013.01); *C07D 207/14* (2013.01); *C07D 401/12* (2013.01); *C07D 401/14* (2013.01); *C07D 403/14* (2013.01); *C07D 487/04* (2013.01); *C07D 498/04* (2013.01)

(58) Field of Classification Search
CPC .................................................. C07D 487/04
See application file for complete search history.

(56) References Cited

U.S. PATENT DOCUMENTS 6,867,221 B2    3/2005    Kodama et al.
2008/0300268 A1   12/2008   Singh et al.

FOREIGN PATENT DOCUMENTS

| | | |
|---|---|---|
| CN | 103183673 A | 7/2013 |
| WO | 0177073 A1 | 10/2001 |
| WO | 2007050522 A1 | 5/2007 |
| WO | 2009026197 A1 | 2/2009 |
| WO | 2009129365 A1 | 10/2009 |
| WO | 2009129370 A1 | 10/2009 |
| WO | 2009129371 A1 | 10/2009 |
| WO | 2013030218 A1 | 3/2013 |
| WO | 2015017502 A1 | 2/2015 |
| WO | 2015179190 A1 | 11/2015 |
| WO | 2015183987 A1 | 12/2015 |
| WO | 2016019237 A2 | 2/2016 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017/141036 A1 | 8/2017 |
| WO | 2017/149313 A1 | 9/2017 |
| WO | 2017/158381 A1 | 9/2017 |
| WO | 2017/158388 A1 | 9/2017 |

(Continued)

OTHER PUBLICATIONS

The International Search Report and Written Opinion, dated Oct. 11, 2018, in the corresponding PCT Appl. No. PCT/GB2018/051454.

(Continued)

*Primary Examiner* — Brian E McDowell

(57) ABSTRACT

The present invention relates to a class of sulfonamide-substituted cyanopyrrolidines of Formula (Ia) and (Ib) with activity as inhibitors of deubiquitilating enzymes, in particular, ubiquitin C-terminal hydrolase L1 (UCHL1) and ubiquitin C-terminal hydrolase 30 or ubiquitin specific peptidase 30 (USP30), having utility in a variety of therapeutic areas including cancer and conditions involving mitochondrial dysfunction: (Formulae (Ia), (Ib)).

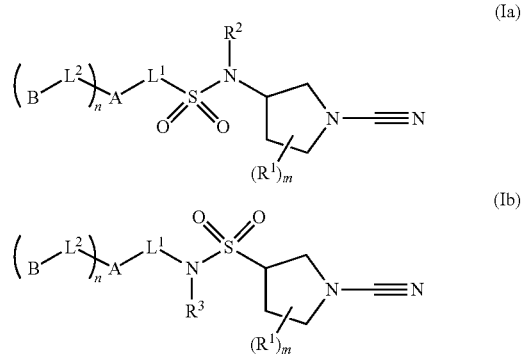

14 Claims, No Drawings

(56) References Cited

FOREIGN PATENT DOCUMENTS

| WO | 2017/163078 A1 | 9/2017 |
|---|---|---|
| WO | 2018060689 A1 | 4/2018 |
| WO | 2018060691 A1 | 4/2018 |
| WO | 2018060742 A1 | 4/2018 |
| WO | 2018065768 A1 | 4/2018 |
| WO | 2018234775 A1 | 12/2018 |

OTHER PUBLICATIONS

Falgueyret et al., "Novel, Nonpeptidic Cyanamides as Potent and Reversible Inhibitors of Human Cathepsins K and L," J. Med. Chem. 2001, 44, 94-104.

Laine et al., "Discovery of Novel Cyanamide-Based Inhibitors of Cathepsin C," ACS Med. Chem. Lett. 2011, 2, 142-147.

Komander et al., "Breaking the chains: structure and function of the deubiquitinases". Nature Reviews Molecular Cell Biology, 10, 550-563, 2009.

Rydzewski et al., "Peptidic 1-Cyanopyrrolidines: Synthesis and SAR of a Series of Potent, Selective Cathepsin Inhibitors", Bioorganic & Medicinal Chemistry 10 (2002) 3277-3284.

Deaton et al., "Novel and potent cyclic cyanamide-based cathepsin K inhibitors", Bioorganic & Medicinal Chemistry Letters 15 (2005) 1815-1819.

Oballa et al., "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

Nakamura et al., "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al., "The mitochondrial deubiquitinase USP30 opposes parkin-mediated mitophagy", Nature vol. 510, 370-375, 2014.

Liang et al., "USP30 deubiquitylates mitochondrial Parkin substrates and restricts apoptotic cell death", EMBO Reports, 1-10, 2015; DOI 10.15252/embr.201439820.

Bedford et al., "Ubiquitin-like protein conjugation and the ubiquitin—proteasome system as drug targets," Nat Rev Drug Discov. Jan. 2011;10(1):29-46.

Zheng et al., "Heterogeneous expression and biological function of ubiquitin carboxy-terminal hydrolase-L1 in osteosarcoma". Cancer Letters, 359, 36-46, 2015.

Ward et al., "Quantitative Chemical Proteomic Profiling of Ubiquitin Specific Proteases in Intact Cancer Cells," ACS Chem. Biol. 2016, 11, 3268-3272.

Aurich. H.G. et al., "Enantiomerically Pure 3-Oxa-2.7-diazabicyclo[3.3.0]octanes: Preparation, Analysis of Conformation and Test for Enantioselective Catalysis", Tetrahedron, Elsevier, vol. 51 No. 38, Jan. 1, 1995, pp. 10497-10512.

Clague et al., "Deubiquitylases from genes to organism", Physiol. Rev. 93:1289-1315, 2013.

Hurst-Kennedy et al., "Ubiquitin C-terminal hydrolast L1 in tumorigenesis", Hindawi publishing corporation, Biochem. Res. Int'l., 2012: 1-10, 2012.

Hussain et al., "The de-ubiquitinase UCH-L1 is an oncogene that drives the development of lymphoma in vivo by deregulating PHLPP1 and Akt signaling", Leukemia 24:1641-1655, 2010.

Song J et al., "Synthesis and Biochemical Evaluation of Thiochromanone Thiosemicarbazone Analogues as Inhibitors at Cathepsin L", ACS Med. Chem. Lett. 2012, 3, 450-453.

Wynn, T.A., "Fibrotic Disease and the TH1/TH2 Paradigm", Nat Rev Immunol. Aug. 2004; 4(8): 583-594.

SULFONAMIDE-SUBSTITUTED CYANOPYRROLIDINES WITH ACTIVITY AS DUB INHIBITORS

This application is a National Stage Application of PCT/GB2018/051454 filed May 30, 2018, which claims priority from UK Patent Application No. 1708652.1 filed on May 31, 2017. The priority of said PCT and UK Patent Application are claimed. Each of the prior mentioned applications is hereby incorporated by reference herein in its entirety.

The present invention relates to a class of sulfonamide-substituted cyanopyrrolidines with activity as inhibitors of deubiquitilating enzymes, in particular, ubiquitin C-terminal hydrolase L1 (UCHL1) and ubiquitin C-terminal hydrolase 30 or ubiquitin specific peptidase 30 (USP30), uses thereof, processes for the preparation thereof and composition containing said inhibitors. These inhibitors have utility in a variety of therapeutic areas including cancer and conditions involving mitochondrial dysfunction.

Ubiquitin is a small protein consisting of 76 amino acids that can be reversibly attached to protein substrates. Protein ubiquitylation regulates many cellular functions including cell cycle progression, apoptosis, modification of cell surface receptors, regulation of DNA transcription and DNA repair. Thus, the ubiquitin proteasome system has been implicated in the pathogenesis of numerous disease states including inflammation, viral infection, metabolic dysfunction, CNS disorders, and oncogenesis (Clague et al., Physiol Rev 93:1289-1315, 2013).

Ubiquitin and ubiquitin-like proteins (Ubls) are cleaved from protein substrates by isopeptidases called deubiquity-lating enzymes (DUBs). There are approximately 100 DUBs in human cells, divided into sub-families based on sequence homology: ubiquitin C-terminal hydrolases (UCHs), ubiquitin-specific proteases (USPs), ovarian tumour proteases (OTUs), Machado-Josephin domain proteases (MJDs), JAB1/MPN/MOV34 metalloproteases (JAMMs) or Sentrin-specific proteases (SENPs). The UCH family consisting of UCHL1, UCHL3, UCHL5 and BAP1 are cysteine proteases that operate through an active site thiol. UCHs are believed to preferentially cleave small protein substrates and to be involved in the processing and recycling of ubiquitin (Komander et al., Nat Rev Mol Cell Biol 10:550-563, 2009).

UCHL1 is a 223-amino acid protein whose expression is normally limited to the brain, peripheral nervous system, ovaries and testis in mammals. However, expression of UCHL1 has been reported to be up-regulated in several pathological conditions including cancer. Transgenic mice over-expressing UCHL1 are prone to malignancy, primarily lymphomas and lung tumours, demonstrating that UCHL1 is an oncogene (Hussain et al., Leukemia 24:1641-1655, 2010). The oncogenic function of UCHL1 is further supported by clinical studies demonstrating that UCHL1 expression in tumours (including breast, colorectal, osteosarcoma and pancreatic) is inversely correlated with patient survival (Hurst-Kennedy et al., Biochem Res Int, 2012, Zheng et al., Cancer Lett 359:36-46). Thus, pharmacological inhibition of UCHL1 would serve as novel treatment for such cancers.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate several mitochondrial proteins, until recently, deubiquitylating enzymes remained elusive. USP30 is a 517-amino acid protein which is found in the mitochondrial outer membrane. It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of several proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteasome, such as DUBs, are predicted to be better tolerated (Bedford et al., Nature Rev 10:29-46, 2011).

Fibrotic diseases, including renal, hepatic and pulmonary fibrosis, are a leading cause of morbidity and mortality and can affect all tissues and organ systems. Fibrosis is considered to be the result of acute or chronic stress on the tissue or organ, characterized by extracellular matrix deposition, reduction of vascular/tubule/duct/airway patency and impairment of function ultimately resulting in organ failure. Many fibrotic conditions are promoted by lifestyle or environmental factors; however, a proportion of fibrotic conditions can be initiated through genetic triggers or indeed are considered idiopathic (i.e. without a known cause). Certain fibrotic disease, such as idiopathic pulmonary fibrosis (IPF), can be treated with non-specific kinase inhibitor (nintedanib) or drugs without a well-characterized mechanism of action (pirfenidone). Other treatments for organ fibrosis, such as kidney or liver fibrosis, alleviate pressure on the organ itself (e.g. beta blockers for cirrhosis, angiotensin receptor blockers for chronic kidney disease). Attention to lifestyle factors, such as glucose and diet control, may also influence the course and severity of disease. Preclinical models are available to study potential novel therapeutics, through their ability to model fibrosis pathology (e.g. collagen deposition) consistent with the human condition. Preclinical models can be toxin-mediated (e.g. bleomycin for lung and skin fibrosis), surgical (e.g. unilateral ureter obstruction model for acute tubulointerstitial fibrosis), and genetic (e.g. diabetic (db/db) mice for diabetic nephropathy). For example, both examples previously given for indicated IPF treatments (nintedanib and pirfenidone) show efficacy in the bleomycin lung fibrosis model.

Mitochondrial dysfunction has been implicated in a number of fibrotic diseases, with oxidative stress downstream of dysfunction being the key pathogenic mediator, alongside decreased ATP production. In preclinical models, disruption of the mitophagy pathway (through mutation or knockout of either parkin or PINK1) exacerbates lung fibrosis and kidney fibrosis, with evidence of increased oxidative stress.

Accordingly, there is a need for compounds that are inhibitors of one or more DUBs such as UCHL1 and USP30, for the treatment of indications where inhibition of USP30 or UCHL1 is indicated.

Series of derivatives of cyano-substituted heterocycles are disclosed as deubiquitylating enzyme inhibitors in PCT applications WO 2016/046530, WO 2016/156816, WO 2017/009650, WO 2017/093718, WO 2017/103614, WO 2017/149313, WO 2017/109488, WO 2017/141036, WO 2017/163078, WO 2017/158381, WO 2017/158388, PCT/GB2017/052971, PCT/GB2017/052949, PCT/GB2017/052880, and PCT/GB2017/052882. Falgueyret et al., J. Med. Chem. 2001, 44, 94-104, and PCT application WO 01/77073 refer to cyanopyrrolidines as inhibitors of Cathepsins K and L, with potential utility in treating osteoporosis and other bone-resorption related conditions. PCT application WO 2015/179190 refers to N-acylethanolamine hydrolysing acid amidase inhibitors, with potential utility in treating ulcerative colitis and Crohn's disease. PCT application WO 2013/030218 refers to quinazolin-4-one compounds as inhibitors of ubiquitin specific proteases, such as USP7, with potential utility in treating cancer, neurodegenerative diseases, inflammatory disorders and viral infections. PCT applications WO 2015/017502 and WO 2016/019237 refer to inhibitors of Bruton's tyrosine kinase with potential utility in treating disease such as autoimmune disease, inflammatory disease and cancer. Laine et al., ACS Med Chem Lett., 2011, 2, 132-147, and PCT applications WO 2009/026197, WO 2009/129365, WO 2009/129370, and WO 2009/129371, refer to cyanopyrrolidines as inhibitors of Cathepsin C with potential utility in treating COPD. United States patent application US 2008/0300268 refers to polyaromatic compounds as inhibitors of tyrosine kinase receptor PDGFR. Song et al., ACS Med Chem Lett., 2012, 3, 450-453 refers to Cathepsin L inhibitors. Lonergan D., PCT application WO 2015/183987, refers to pharmaceutical compositions comprising deubiquitinase inhibitors and human serum albumin in methods of treating cancer, fibrosis, an autoimmune disease or condition, an inflammatory disease or condition, a neurodegenerative disease or condition or an infection. Lonergan notes that deubiquitinases, including UCHL5/UCH37, USP4, USP9X, USP11 and USP15, are said to have been implicated in the regulation of the TGF-beta signalling pathway, the disruption of which gives rise to neurodegenerative and fibrotic diseases, autoimmune dysfunction and cancer.

According to a first aspect, the present invention provides a compound of formula (I), which is selected from (Ia) and (Ib):

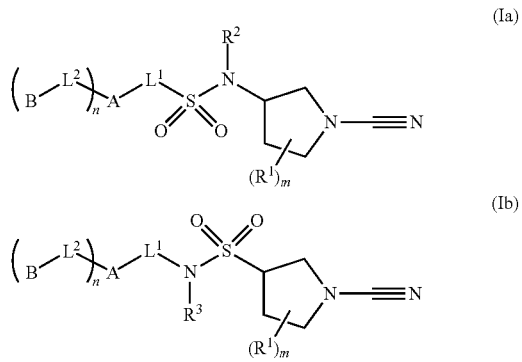

a tautomer thereof, or a pharmaceutically acceptable salt of said compound or tautomer, wherein:

m is 0 to 4;

n is 0 or 1;

each $R^1$ is independently selected from halo, cyano, hydroxy, $(C_1-C_6)$alkyl, $(C_1-C_6)$alkoxy, halo$(C_1-C_6)$alkyl, halo$(C_1-C_6)$alkoxy, and $(C_1-C_6)$alkoxy$(C_1-C_6)$alkyl;

$R^2$ and $R^3$ are selected from hydrogen, $(C_1-C_6)$alkyl, and $(C_1-C_6)$alkoxy$(C_1-C_6)$alkyl; or where $R^1$ and $NR^2$ are situated on adjacent ring atoms, $R^1$ together with $R^2$ may form a 5 to 6-membered heterocyclic ring containing 1 to 2 heteroatoms independently selected from N, O and S, at least one of which is N;

$L^1$ is selected from a covalent bond, $(C_1-C_4)$alkylene, and $(C_2-C_4)$alkenylene;

$L^2$ is selected from a covalent bond, $(C_1-C_4)$alkylene, $(C_2-C_4)$alkenylene, and $(C_0-C_3)$alkylene-X—$(C_0-C_3)$alkylene;

X is selected from O, S, SO, $SO_2$, $NR^4$, $NR^4C(O)$, $C(O)NR^4$, $NR^4C(O)NR^5$, $C(O)$, $C(O)O$, $CO(O)$, $XO(O)O$, $SO_2NR^4$, $NR^4SO_2$, and $NR^4SO_2NR^5$;

$R^4$ and $R^5$ are each independently selected from hydrogen, $(C_1-C_6)$alkyl, and $(C_1-C_6)$alkoxy$(C_1-C_6)$alkyl;

group 'A' is selected from a 3 to 10-membered carbocyclic ring, and a 3 to 10-membered heterocyclic ring comprising 1 to 4 heteroatoms independently selected from N, O, and S; with the proviso that for the compound of formula (Ia) when $L^1$ is a covalent bond, 'A' is linked to the sulfonamide via a ring C-atom;

or A-$L^1$-N—$R^3$ may optionally form a 3 to 10-membered heterocyclic ring comprising 1 to 4 heteroatoms independently selected from N, O, and S, at least one of which is N;

group 'B' is selected from a 3 to 10-membered carbocyclic ring, and a 3 to 10-membered heterocyclic ring comprising 1 to 4 heteroatoms independently selected from N, O, and S; and each carbocyclic and heterocyclic ring may be optionally substituted with 1 to 4 substituents independently selected from halo, cyano, hydroxy, oxo, $(C_1-C_6)$alkyl, $(C_1-C_6)$alkoxy, $(C_1-C_6)$alkoxy$(C_1-C_6)$alkyl, halo$(C_1-C_6)$alkyl, halo ($C_1$-$C_6$)alkoxy, NH($C_1$-$C_6$)alkyl, N(($C_1$-$C_6$)alkyl)$_2$, C(O)NH($C_1$-$C_6$)alkyl, C(O)N($C_1$-$C_6$)alkyl)$_2$, NHC(O)($C_1$-$C_6$)alkyl, N($C_1$-$C_6$)alkyl)C(O)($C_1$-$C_6$)alkyl), C(O)($C_1$-$C_6$)alkyl, C(O)O($C_1$-$C_6$)alkyl, $CO_2H$, $CONH_2$, $SO_2NH$($C_1$-$C_6$)alkyl, and $SO_2N$(($C_1$-$C_6$)alkyl)$_2$;

for use in the treatment of a disorder or condition where inhibition of USP30 or UCH L1 is known, or can be shown, to produce a beneficial effect, in a mammal.

Unless otherwise indicated, alkyl, alkenyl, and alkoxy groups, including the corresponding divalent radicals, may be straight or branched and contain 1 to 6 carbon atoms and typically 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Halo means fluoro, chloro, bromo or iodo, in particular, fluoro or chloro.

Haloalkyl and haloalkoxy groups may contain one or more halo substituents. Examples are trifluoromethyl and trifluoromethoxy.

A carbocyclic ring may be monocyclic or bicyclic, saturated, partially saturated or aromatic. Examples of carbocyclic groups are cyclopropyl, cyclopentyl, cyclohexyl, indanyl, indenyl, naphthyl, phenyl, tetrahydrofuranyl, tetrahydropyranyl, and tetralinyl.

A heterocyclic ring may be monocyclic or bicyclic, including fused-bicyclic, saturated, partially saturated or aromatic. Examples of heterocyclic groups are azetidinyl, furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiazolidinyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl, thiazolinyl, benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl, isoindolinyl, isoindolyl, tetrahydroisoquinolinyl, and tetrahydropyrazolopyrazinyl.

Unless otherwise indicated, the term substituted means substituted by one or more defined groups. In the case where groups may be selected from more than one alternatives, the selected groups may be the same or different. The term independently means that where more than one substituent is selected from more than one possible substituents, those substituents may be the same or different.

Preferred embodiments of the compound of formula (I) for use in the present invention are defined below.

Preferably, m is selected from 0, 1, 2, 3 and 4.

More preferably, m is 0, 1 or 2.

Preferably, each $R^1$ is independently selected from halo, cyano, hydroxy, methyl, ethyl, isopropyl, methoxy, ethoxy, methoxymethyl, and methoxyethyl.

More preferably, $R^1$ is independently selected from fluoro, cyano, methyl, and methoxy.

Preferably, $R^2$ and $R^3$ are selected from hydrogen, methyl, ethyl, isopropyl, methoxy, ethoxy, methoxymethyl, and methoxyethyl.

More preferably, $R^2$ and $R^3$ are selected from hydrogen and methyl.

In the compound of formula (Ia), one of the $R^1$ groups and $NR^2$ may be situated on adjacent ring atoms. In this embodiment, said $R^1$ together with $R^2$ may form a 5 to 6-membered heterocyclic ring containing 1 to 2 heteroatoms independently selected from N, O and S, at least one of which is N.

Preferably, $R^1$ together with $R^2$ forms a 5 to 6-membered heterocyclic ring containing 1 to 2 heteroatoms independently selected from N and 0, at least one of which is N.

More preferably, $R^1$ together with $R^2$ forms a morpholine, piperidine, or pyrrolidine ring. Preferably, $L^1$ is selected from a covalent bond, methylene, ethylene, propylene, isopropylene, ethenyl, and allyl.

More preferably, $L^1$ is selected from a covalent bond, methylene, and ethylene.

Preferably, $L^2$ is selected from a covalent bond, methylene, ethylene, propylene, isopropylene, ethenyl, allyl, and ($C_0$-$C_1$)alkylene-X—($C_0$-$C_1$)alkylene.

Preferably, X is selected from O, $NR^4$, $NR^4C(O)$, and $C(O)NR^4$.

Preferably, $R^4$ and $R^5$ are each independently selected from hydrogen, methyl, ethyl, isopropyl, methoxy, ethoxy, methoxymethyl, and methoxyethyl.

More preferably, $R^4$ and $R^5$ are each independently selected from hydrogen and methyl.

Most preferably, $L^2$ is selected from a covalent bond, an oxygen atom, methylene, $OCH_2$, and NHC(O).

In one preferred embodiment, group 'A' is an optionally substituted ring selected from a 6 to 10-membered carbocyclic ring, and a 5 to 10-membered heterocyclic ring comprising 1 to 3 heteroatoms independently selected from N, O, and S.

More preferably, group 'A' is an optionally substituted ring selected from indanyl, phenyl, tetrahydrofuranyl, tetrahydropyranyl, tetralinyl, benzothiazolyl, imidazolyl, isoxazolyl, piperidinyl, pyrazolyl, pyridyl, pyrimidinyl, thiazolyl, 1,2,4-triazolyl, and quinolinyl.

In another preferred embodiment, A-$L^1$-N—$R^3$ forms an optionally-substituted 4 to 10-membered heterocyclic ring comprising 1 to 3 heteroatoms independently selected from N, O, and S, at least one of which is N.

More preferably, A-$L^1$-N—$R^3$ forms an optionally substituted ring selected from azetidinyl, isoindolinyl, piperazinyl, piperidinyl, tetrahydroisoquinolinyl, and 4,5,6,7-tetrahydropyrazolo[1,5-a]pyrazinyl.

Preferably, each carbocyclic and heterocyclic ring of group 'A' and the ring formed from A-$L^1$-N—$R^3$, may be optionally substituted with 1 to 4 substituents independently selected from halo, cyano, hydroxy, oxo, ($C_1$-$C_6$)alkyl, ($C_1$-$C_6$)alkoxy, ($C_1$-$C_6$)alkoxy($C_1$-$C_6$)alkyl, halo($C_1$-$C_6$)alkyl, halo($C_1$-$C_6$)alkoxy, and NHC(O)($C_1$-$C_6$)alkyl.

More preferably, the optional substituents of group 'A' and the ring formed from A-$L^1$-N—$R^3$, are independently selected from halo, cyano, hydroxy, oxo, methyl, ethyl, isopropyl, methoxy, ethoxy, methoxymethyl, trifluoromethyl, trifluoromethoxy, and NHC(O)isobutyl.

Most preferably, group 'A' and the ring formed from A-$L^1$-N—$R^3$, may be optionally substituted with 1 to 2 substituents independently selected from chloro, fluoro, cyano, methyl, isopropyl, methoxy, trifluoromethyl, trifluoromethoxy, and NHC(O)isobutyl.

Preferably, group 'B' is an optionally substituted ring selected from a 6 to 10-membered carbocyclic ring, and a 5 to 10-membered heterocyclic ring comprising 1 to 4 heteroatoms independently selected from N, O, and S.

More preferably, group B' is an optionally substituted ring selected from phenyl, and a 5 to 6-membered heterocyclic ring comprising 1 to 3 heteroatoms independently selected from N, O, and S.

Yet more preferably, group 'B' is an optionally substituted ring selected from phenyl, oxazolyl, piperazinyl, piperidinyl, pyrazolyl, pyridyl, pyrimidinyl, pyrrolidinyl, 1,2-thiazolidinyl, and thiazolyl.

Preferably, each carbocyclic and heterocyclic ring of group 'B' may be optionally substituted with 1 to 4 substituents independently selected from halo, cyano, hydroxy, oxo, $(C_1-C_6)$alkyl, $(C_1-C_6)$alkoxy, $(C_1-C_6)$alkoxy$(C_1-C_6)$alkyl, halo$(C_1-C_6)$alkyl, halo$(C_1-C_6)$alkoxy.

More preferably, the optional substituents of group '13' are independently selected from halo, cyano, hydroxy, oxo, methyl, ethyl, isopropyl, methoxy, ethoxy, methoxymethyl, trifluoromethyl, and trifluoromethoxy.

Most preferably, group 'B' may be optionally substituted with 1 to 2 substituents independently selected from chloro, fluoro, oxo, methyl, methoxy, and $CF_3$.

According to one preferred embodiment, the compound of formula (I) for use in the present invention is a compound of formula (Ia):

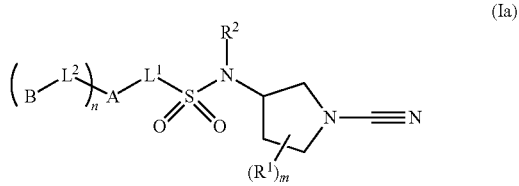

(Ia)

a tautomer thereof, or a pharmaceutically acceptable salt of said compound or tautomer, wherein:
  m is 0, 1 or 2;
  n is 0 or 1;
  each $R^1$ is independently selected from fluoro, cyano, methyl, and methoxy;
  $L^1$ is selected from a covalent bond, methylene, and ethylene;
  $L^2$ is selected from a covalent bond, an oxygen atom, methylene, $OCH_2$, and NHC(O);
  group 'A' is selected from a 6 to 10-membered carbocyclic ring, and a 5 to 10-membered heterocyclic ring comprising 1 to 3 heteroatoms independently selected from N, O, and S, each of which may be optionally substituted with 1 to 2 substituents independently selected from chloro, fluoro, cyano, methyl, isopropyl, methoxy, trifluoromethyl, trifluoromethoxy, and NHC(O)isobutyl; and
  group 'B' is selected from phenyl, and a 5 to 6-membered heterocyclic ring comprising 1 to 3 heteroatoms independently selected from N, O, and S, each of which may be optionally substituted with 1 to 2 substituents independently selected from chloro, fluoro, oxo, methyl, methoxy, and $CF_3$.

According to another preferred embodiment, the compound of formula (I) for use in the present invention is a compound of formula (Ia):

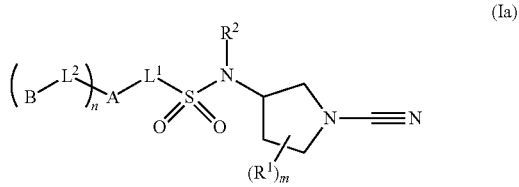

(Ia)

a tautomer thereof, or a pharmaceutically acceptable salt of said compound or tautomer, wherein:

m is 1 or 2;
  n is 0 or 1;
  one of the $R^1$ groups and $NR^2$ are situated on adjacent ring atoms, and said $R^1$ together with $R^2$ forms a 5 to 6-membered heterocyclic ring containing 1 to 2 heteroatoms independently selected from N, O and S, at least one of which is N;
  the other, optional $R^1$ is selected from fluoro, cyano, methyl, and methoxy;
  $L^1$ is selected from a covalent bond, methylene, and ethylene;
  $L^2$ is selected from a covalent bond, an oxygen atom, methylene, $OCH_2$, and NHC(O);
  group 'A' is selected from a 6 to 10-membered carbocyclic ring, and a 5 to 10-membered heterocyclic ring comprising 1 to 3 heteroatoms independently selected from N, O, and S, each of which may be optionally substituted with 1 to 2 substituents independently selected from chloro, fluoro, cyano, methyl, isopropyl, methoxy, trifluoromethyl, trifluoromethoxy, and NHC(O)isobutyl; and
  group 'B' is selected from phenyl, and a 5 to 6-membered heterocyclic ring comprising 1 to 3 heteroatoms independently selected from N, O, and S, each of which may be optionally substituted with 1 to 2 substituents independently selected from chloro, fluoro, oxo, methyl, methoxy, and $CF_3$.

According to another preferred embodiment, the compound of formula (I) for use in the present invention is a compound of formula (Ib):

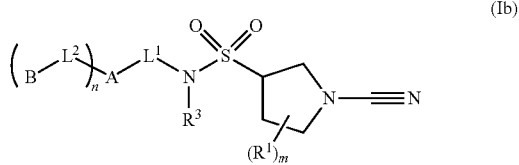

(Ib)

a tautomer thereof, or a pharmaceutically acceptable salt of said compound or tautomer, wherein:
  m is 0, 1 or 2;
  n is 0 or 1;
  each $R^1$ is independently selected from fluoro, cyano, methyl, and methoxy;
  $L^2$ is selected from a covalent bond, an oxygen atom, methylene, $OCH_2$, and NHC(O); A-$L^1$-N—$R^3$ forms a 4 to 10-membered heterocyclic ring comprising 1 to 3 heteroatoms independently selected from N, O, and S, at least one of which is N, which may be optionally substituted with 1 to 2 substituents independently selected from chloro, fluoro, cyano, methyl, isopropyl, methoxy, trifluoromethyl, trifluoromethoxy, and NHC(O)isobutyl; and group 'B' is selected from phenyl, and a 5 to 6-membered heterocyclic ring comprising 1 to 3 heteroatoms independently selected from N, O, and S, each of which may be optionally substituted with 1 to 2 substituents independently selected from chloro, fluoro, oxo, methyl, methoxy, and $CF_3$.

Preferred compounds of formula (I) for use in the present invention are selected from:
N-(1-cyanopyrrolidin-3-yl)-[1,1'-biphenyl]-2-sulfonamide (Ex. 1);
N-(1-cyanopyrrolidin-3-yl)-[1,1'-biphenyl]-4-sulfonamide (Ex. 2);
(R)—N-(1-cyanopyrrolidin-3-yl)-[1,1'-biphenyl]-4-sulfonamide (Ex. 3);
(S)—N-(1-cyanopyrrolidin-3-yl)-[1,1'-biphenyl]-4-sulfonamide (Ex. 4);

N-(1-cyanopyrrolidin-3-yl)benzenesulfonamide (Ex. 5);
(S)—N-(1-cyanopyrrolidin-3-yl)benzenesulfonamide (Ex. 6);
(R)—N-(1-cyanopyrrolidin-3-yl)benzenesulfonamide (Ex. 7);
(4-(benzyloxy)-N-(1-cyanopyrrolidin-3-yl)benzenesulfonamide (Ex. 8);
N-(1-cyanopyrrolidin-3-yl)-4-(pyrimidin-5-yl)benzenesulfonamide (Ex. 9);
N-(1-cyanopyrrolidin-3-yl)-4-(4-methylpiperazin-1-yl)benzenesulfonamide (Ex. 10);
N-(1-cyanopyrrolidin-3-yl)-5-phenylpyridine-2-sulfonamide (Ex. 11);
N-(1-cyanopyrrolidin-3-yl)-4'-fluoro-[1,1'-biphenyl]-4-sulfonamide (Ex. 12);
N-(1-cyanopyrrolidin-3-yl)-4-(pyridin-4-yl)benzenesulfonamide (Ex. 13);
N-(1-cyanopyrrolidin-3-yl)-4-(piperidin-1-yl)benzenesulfonamide (Ex. 14);
N-(1-cyanopyrrolidin-3-yl)-4-(1-methyl-1H-pyrazol-4-yl)benzenesulfonamide (Ex. 15);
N-(1-cyanopyrrolidin-3-yl)-6-phenoxypyridine-3-sulfonamide (Ex. 16);
N-(1-cyanopyrrolidin-3-yl)-5-fluoro-2-methylbenzenesulfonamide (Ex. 17);
N-(1-cyanopyrrolidin-3-yl)-4-isopropylbenzenesulfonamide (Ex. 18);
N-(1-cyanopyrrolidin-3-yl)-4-((5-(trifluoromethyl)pyridin-2-yl)oxy)benzenesulfonamide (Ex. 19);
(R)—N-(1-cyanopyrrolidin-3-yl)-N-methyl-4-(pyridin-3-yl)benzenesulfonamide (Ex. 20);
(3aR,6aR)-1-((4-(pyridin-3-yl)phenyl)sulfonyl)hexahydropyrrolo[3,4-b]pyrrole-5(1H)-carbonitrile (Ex. 21);
rac-(4aR,7aR)-4-tosylhexahydropyrrolo[3,4-b][1,4]oxazine-6(2H)-carbonitrile (Ex. 22);
rac-(4aR,7aS)-4-((4-methylbenzyl)sulfonyl)hexahydropyrrolo[3,4-b][1,4]oxazine-6(2H)-carbonitrile (Ex. 23);
N-(5-(N-(1-cyanopyrrolidin-3-yl)sulfamoyl)pyridin-2-yl)-1-methyl-1H-pyrazole-5-carboxamide (Ex. 24);
N-(1-cyanopyrrolidin-3-yl)-N-methyl-4-((5-(trifluoromethyl)pyridin-2-yl)oxy)benzenesulfonamide (Ex. 25);
N-([1,1'-biphenyl]-4-yl)-1-cyanopyrrolidine-3-sulfonamide (Ex. 26);
3-((4-(4-fluorophenyl)piperazin-1-yl)sulfonyl)pyrrolidine-1-carbonitrile (Ex. 27);
(3-((4-(pyridin-2-yl)piperazin-1-yl)sulfonyl)pyrrolidine-1-carbonitrile (Ex. 28);
3-((4-(pyrimidin-2-yl)piperazin-1-yl)sulfonyl)pyrrolidine-1-carbonitrile (Ex. 29);
3-((4-(4-chlorophenyl)piperidin-1-yl)sulfonyl)pyrrolidine-1-carbonitrile (Ex. 30);
(S)-3-((4-(4-chlorophenyl)piperidin-1-yl)sulfonyl)pyrrolidine-1-carbonitrile (Ex. 31);
(R)-3-((4-(4-chlorophenyl)piperidin-1-yl)sulfonyl)pyrrolidine-1-carbonitrile (Ex. 32);
3-((4-benzylpiperidin-1-yl)sulfonyl)pyrrolidine-1-carbonitrile (Ex. 33);
3-((3-(4-chlorophenyl)azetidin-1-yl)sulfonyl)pyrrolidine-1-carbonitrile (Ex. 34);
(S)-3-((3-(4-chlorophenyl)azetidin-1-yl)sulfonyl)pyrrolidine-1-carbonitrile (Ex. 35);
(R)-3-((3-(4-chlorophenyl)azetidin-1-yl)sulfonyl)pyrrolidine-1-carbonitrile (Ex. 36); and
3-((3-phenoxyazetidin-1-yl)sulfonyl)pyrrolidine-1-carbonitrile (Ex. 37);
a tautomer thereof, or a pharmaceutically acceptable salt of said compound or tautomer.

According to a second aspect, the present invention provides a compound of formula (Ia) selected from (i), (ii), (iii), (iv), and (v):

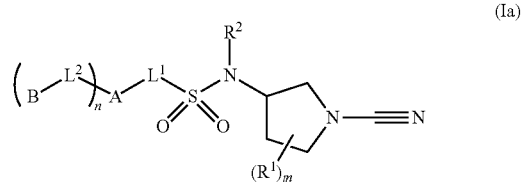

as defined herein in respect of the first aspect of the invention and preferred embodiments thereof, a tautomer thereof, or a pharmaceutically acceptable salt of said compound or tautomer, wherein:
(i) m is 1 to 4; and
one of the $R^1$ groups and $NR^2$ are situated on adjacent ring atoms, and said $R^1$ together with $R^2$ forms a 5 to 6-membered heterocyclic ring containing 1 to 2 heteroatoms independently selected from N, O and S, at least one of which is N;
(ii) n is 0; and
group 'A' is a 3 to 10-membered heterocyclic ring comprising 1 to 4 heteroatoms independently selected from N, O, and S; with the proviso that for the compound of formula (Ia) when $L^1$ is a covalent bond, 'A' is linked to the sulfonamide via a ring C-atom;
with the proviso that
(a) when m is 0; $R^2$ is selected from $(C_1-C_6)$alkyl and $(C_1-C_6)$alkoxy$(C_1-C_6)$alkyl; and is preferably methyl;
(iii) m is 0;
n is 0;
$R^2$ is hydrogen; and
each carbocyclic and heterocyclic ring is substituted with, at least, 1 to 2 substituents independently selected from cyano, hydroxy, oxo, $CF_3$, $OCF_3$, and NHC(O)isobutyl;
(iv) n is 1; and
group 'B' is a substituted 3 to 10-membered heterocyclic ring comprising 1 to 4 heteroatoms independently selected from N, O, and S;
(v) n is 0; and
group 'A' is a 3 to 10-membered heterocyclic ring comprising 1 to 4 heteroatoms independently selected from N, O, and S; with the proviso that for the compound of formula (Ia) when $L^1$ is a covalent bond, 'A' is linked to the sulfonamide via a ring C-atom;
with the proviso that
(a) when m is 0; $R^2$ is hydrogen; and
(b) when m is 1 to 4; $R^2$ is selected from $(C_1-C_6)$alkyl, and $(C_1-C_6)$alkoxy$(C_1-C_6)$alkyl; and is preferably methyl.
In a preferred embodiment of the second aspect of the invention for the compounds of formula (Ia): (i), (ii), (iii), (iv) and (v):
$L^1$ is selected from a covalent bond, methylene, and ethylene; and
$L^2$ is a covalent bond.
In a preferred embodiment of the second aspect of the invention for the compound of formula (Ia)(i):
m is 1;
$L^1$ is selected from a covalent bond, methylene, and ethylene.
$L^2$ is a covalent bond;
group 'A' is phenyl;
group 'B' is pyridyl;

each phenyl and pyridyl ring may be optionally substituted with 1 to 2 substituents independently selected from chloro, fluoro, cyano, hydroxy, methyl, isopropyl, methoxy, $CF_3$, $OCF_3$, NHC(O)isobutyl.

In a preferred embodiment of the second aspect of the invention for the compound of formula (Ia)(iv):

group 'B' is substituted with 1 to 2 substituents independently selected from chloro, fluoro, oxo, methyl, methoxy, and $CF_3$.

Preferred compounds of formula (I) according to the second aspect of the invention are selected from:

N-(1-cyanopyrrolidin-3-yl)-[1,1'-biphenyl]-2-sulfonamide (Ex. 1);
N-(1-cyanopyrrolidin-3-yl)-[1,1'-biphenyl]-4-sulfonamide (Ex. 2);
(R)—N-(1-cyanopyrrolidin-3-yl)-[1,1'-biphenyl]-4-sulfonamide (Ex. 3);
(S)—N-(1-cyanopyrrolidin-3-yl)-[1,1'-biphenyl]-4-sulfonamide (Ex. 4);
(4-(benzyloxy)-N-(1-cyanopyrrolidin-3-yl)benzenesulfonamide (Ex. 8);
N-(1-cyanopyrrolidin-3-yl)-4-(pyrimidin-5-yl)benzenesulfonamide (Ex. 9);
N-(1-cyanopyrrolidin-3-yl)-4-(4-methylpiperazin-1-yl)benzenesulfonamide (Ex. 10);
N-(1-cyanopyrrolidin-3-yl)-5-phenylpyridine-2-sulfonamide (Ex. 11);
N-(1-cyanopyrrolidin-3-yl)-4-(pyridin-4-yl)benzenesulfonamide (Ex. 13);
N-(1-cyanopyrrolidin-3-yl)-4-(piperidin-1-yl)benzenesulfonamide (Ex. 14);
N-(1-cyanopyrrolidin-3-yl)-4-(1-methyl-1H-pyrazol-4-yl)benzenesulfonamide (Ex. 15);
N-(1-cyanopyrrolidin-3-yl)-6-phenoxypyridine-3-sulfonamide (Ex. 16);
N-(1-cyanopyrrolidin-3-yl)-4-isopropylbenzenesulfonamide (Ex. 18);
N-(1-cyanopyrrolidin-3-yl)-4-((5-(trifluoromethyl)pyridin-2-yl)oxy)benzenesulfonamide (Ex. 19);
(R)—N-(1-cyanopyrrolidin-3-yl)-N-methyl-4-(pyridin-3-yl)benzenesulfonamide (Ex. 20);
(3aR,6aR)-1-((4-(pyridin-3-yl)phenyl)sulfonyl)hexahydropyrrolo[3,4-b]pyrrole-5(1H)-carbonitrile (Ex. 21);
rac-(4aR,7aR)-4-tosylhexahydropyrrolo[3,4-b][1,4]oxazine-6(2H)-carbonitrile (Ex. 22);
rac-(4aR,7aS)-4-((4-methylbenzyl)sulfonyl)hexahydropyrrolo[3,4-b][1,4]oxazine-6(2H)-carbonitrile (Ex. 23);
N-(5-(N-(1-cyanopyrrolidin-3-yl)sulfamoyl)pyridin-2-yl)-1-methyl-1H-pyrazole-5-carboxamide (Ex. 24); and
N-(1-cyanopyrrolidin-3-yl)-N-methyl-4-((5-(trifluoromethyl)pyridin-2-yl)oxy)benzenesulfonamide (Ex. 25);
a tautomer thereof, or a pharmaceutically acceptable salt of said compound or tautomer.

According to a third aspect, the present invention provides compound of formula (Ib):

as defined herein in respect of the first aspect of the invention and preferred embodiments thereof, a tautomer thereof, or a pharmaceutically acceptable salt of said compound or tautomer.

In a preferred embodiment of the third aspect of the invention:

m is 0 or 1;
n is 0 or 1;
each $R^1$ is independently selected from fluoro, cyano, methyl, methoxy, and methoxymethyl;
$R^3$ is selected from hydrogen and methyl;
$L^1$ is selected from a covalent bond, methylene, and ethylene;
$L^2$ is selected from a covalent bond, an oxygen atom, and methylene;
group 'A' is selected from indanyl, phenyl, tetralinyl, benzothiazolyl, piperidinyl, pyrazolyl, pyridyl, pyrimidinyl, thiazolyl, 1,2,4-triazolyl, and quinolinyl;
or $A-L^1-N-R^3$ may form a ring selected from azetidinyl, isoindolinyl, piperazinyl, piperidinyl, tetrahydroisoquinolinyl, and 4,5,6,7-tetrahydropyrazolo[1,5-a]pyrazinyl;
group 'B' is selected from phenyl and pyridyl; and
each carbocyclic and heterocyclic ring may be optionally substituted with 1 to 2 substituents independently selected from chloro, fluoro, hydroxy, and methyl.

Preferred compounds of formula (I) according to the third aspect of the invention are selected from:

N-([1,1'-biphenyl]-4-yl)-1-cyanopyrrolidine-3-sulfonamide (Ex. 26);
3-((4-(4-fluorophenyl)piperazin-1-yl)sulfonyl)pyrrolidine-1-carbonitrile (Ex. 27);
(3-((4-(pyridin-2-yl)piperazin-1-yl)sulfonyl)pyrrolidine-1-carbonitrile (Ex. 28);
3-((4-(pyrimidin-2-yl)piperazin-1-yl)sulfonyl)pyrrolidine-1-carbonitrile (Ex. 29);
3-((4-(4-chlorophenyl)piperidin-1-yl)sulfonyl)pyrrolidine-1-carbonitrile (Ex. 30);
(S)-3-((4-(4-chlorophenyl)piperidin-1-yl)sulfonyl)pyrrolidine-1-carbonitrile (Ex. 31);
(R)-3-((4-(4-chlorophenyl)piperidin-1-yl)sulfonyl)pyrrolidine-1-carbonitrile (Ex. 32);
3-((4-benzylpiperidin-1-yl)sulfonyl)pyrrolidine-1-carbonitrile (Ex. 33);
3-((3-(4-chlorophenyl)azetidin-1-yl)sulfonyl)pyrrolidine-1-carbonitrile (Ex. 34);
(S)-3-((3-(4-chlorophenyl)azetidin-1-yl)sulfonyl)pyrrolidine-1-carbonitrile (Ex. 35);
(R)-3-((3-(4-chlorophenyl)azetidin-1-yl)sulfonyl)pyrrolidine-1-carbonitrile (Ex. 36); and
3-((3-phenoxyazetidin-1-yl)sulfonyl)pyrrolidine-1-carbonitrile (Ex. 37);
a tautomer thereof, or a pharmaceutically acceptable salt of said compound or tautomer.

According to a further aspect, the present invention provides a pharmaceutical composition comprising a compound of formula (Ia) or (Ib) according to either the second or third aspects of the invention, or a pharmaceutically acceptable salt of said compound or tautomer, together with a pharmaceutically acceptable diluent or carrier.

Pharmaceutical compositions of this invention comprise any of the compounds of the invention combined with any pharmaceutically acceptable carrier, adjuvant or vehicle. Examples of pharmaceutically acceptable carriers are known to those skilled in the art and include, but are not limited to, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of formula (I) are inhibitors of deubiquitylating enzymes, including in particular, either UCHL1 or USP30, or both.

According to a further aspect, the present invention provides a compound of formula (Ia) or (Ib) according to either the second or third aspects of the invention, a tautomer thereof, or a pharmaceutically acceptable salt of said compound or tautomer for use as a medicament.

According to a further aspect, the present invention provides a method of treatment of a disorder or condition where inhibition of UCHL1 or USP30 is known, or can be shown, to produce a beneficial effect, in a mammal, comprising administering to said mammal a therapeutically effective amount of a compound of formula (I) as defined herein, according to any one of the first, second, and third aspects of the invention, a tautomer thereof, or a pharmaceutically acceptable salt of said compound or tautomer.

According to a further aspect, the present invention provides the use of a compound of formula (I) as defined herein, according to any one of the first, second, and third aspects of the invention, a tautomer thereof, or a pharmaceutically acceptable salt of said compound or tautomer, in the preparation of a medicament for the treatment of a disorder or condition where inhibition of UCHL1 or USP30 is known, or can be shown, to produce a beneficial effect.

In one preferred embodiment of all aspects of the invention, the disorder or condition is one where inhibition of UCHL1 is known, or can be shown, to produce a beneficial effect.

In a more preferred embodiment, the disorder or condition benefiting from UCHL1 activity is selected from cancer, neurodegenerative disorders (such as Alzheimer's disease, Parkinson's disease), chronic obstructive pulmonary disease (COPD), inflammation, viral infections, including MERS or SARS, bacterial infections, including TB, metabolic disorders, and fibrosis. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

Fibrosis refers to the accumulation of extracellular matrix constituents that occurs following trauma, inflammation, tissue repair, immunological reactions, cellular hyperplasia, and neoplasia. Fibrotic disorders that may be treated by the compounds and compositions of the present invention include, inter alia, fibrosis/fibrotic disorders associated with major organ diseases, for example, interstitial lung disease (ILD), liver cirrhosis, non-alcoholic fatty liver disease (NAFLD) and non-alcoholic steatohepatitis (NASH) (hepatic fibrosis), kidney disease (renal fibrosis), heart or vascular disease (cardiac fibrosis) and diseases of the eye; fibroproliferative disorders, for example, systemic and local scleroderma, keloids and hypertrophic scars, atherosclerosis, restenosis, and Dupuytren's contracture; scarring associated with trauma, for example, surgical complications, chemotherapeutics drug-induced fibrosis (e.g. bleomycin-induced fibrosis), radiation-induced fibrosis, accidental injury and burns); retroperitoneal fibrosis (Ormond's disease); and peritoneal fibrosis/peritoneal scarring in patients receiving peritoneal dialysis, usually following renal transplantation. See, for example, Wynn, Thomas A., "Fibrotic disease and the TH1/TH2 paradigm", Nat Rev Immunol. 2004 August; 4(8): 583-594. The present invention therefore relates to methods of treatment, and compounds and compositions used in said methods of fibrosis/fibrotic disorders of and/or associated with the major organs, the lung, liver, kidney, heart, skin, eye, gastrointestinal tract, peritoneum, bone marrow, etc., and other diseases/disorders herein described.

Interstitial lung disease (ILD) includes disorders in which pulmonary inflammation and fibrosis are the final common pathways of pathology, for example, sarcoidosis, silicosis, drug reactions, infections and collagen vascular diseases, such as rheumatoid arthritis and systemic sclerosis (scleroderma). The fibrotic disorder of the lung includes, for example, pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, and bronchiectasis.

Idiopathic pulmonary fibrosis (IPF) is the most common type of ILD and has no known cause.

Liver cirrhosis has similar causes to ILD and includes, for example, cirrhosis associated with viral hepatitis, schistosomiasis and chronic alcoholism.

Kidney disease, may be associated with diabetes, which can damage and scar the kidneys leading to a progressive loss of function, and also hypertensive diseases. Kidney fibrosis may occur at any stage of kidney disease, from chronic kidney disease (CKD) through to end-stage renal disease (ESRD). Kidney fibrosis can develop as a result of cardiovascular disease such as hypertension or diabetes, both of which place immense strain on kidney function which promotes a fibrotic response. However, kidney fibrosis can also be idiopathic (without a known cause), and certain genetic mitochondrial diseases also present kidney fibrosis manifestations and associated symptoms.

Heart disease may result in scar tissue that can impair the ability of the heart to pump. Diseases of the eye include, for example, macular degeneration and retinal and vitreal retinopathy, which can impair vision.

In a preferred embodiment, the present invention is directed to the treatment of Idiopathic pulmonary fibrosis (IPF).

In another preferred embodiment, the present invention is directed to the treatment of kidney fibrosis.

In another preferred embodiment of all aspects of the invention, the disorder or condition is one where inhibition of USP30 is known, or can be shown, to produce a beneficial effect.

In a more preferred embodiment, the disorder or condition benefiting from USP30 activity is selected from cancer and mitochondrial dysfunction. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GMl-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia. The compounds of the invention are useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents. The compounds may be combined with an additional anti-tumour therapeutic agent, for example chemotherapeutic drugs or inhibitors of other regulatory proteins. In one embodiment, the additional anti-tumour therapeutic agent is selected from a PARP (poly ADP ribose polymerase) inhibitor, a BRCA2 inhibitor and an ATM inhibitor. In another embodiment, the PARP (poly ADP ribose polymerase) inhibitor is an inhibitory RNA (RNAi) molecule (PARPi). In a further embodiment, PARP inhibitors may be selected from one or more of Iniparib (BSI 201), Olaparib (AZD-2281), Rucaparib (AG014699, PF-01367338) and Veliparib (ABT-888), MK-4827, CEP-9722, E7016(GPI-21016), LT-673, MP-124, NMS-P118. In a further embodiment, the additional anti-tumour agent is a chemotherapeutic agent. Chemotherapeutic agents may be selected from olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

For compounds of formula (I) where:

n is 0 and group 'A' is a carbocyclic ring optionally substituted by halo; or n is 0, $L^1$ is a bond, and group 'A' is an unsubstituted, saturated heterocyclic ring; or alternatively, for compounds of formula (I) other than those of formula (Ia): (i), (ii), (iii), (iv), and (v):

the use in cancer is preferably a cancer selected from, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

Additionally, or alternatively, for compounds of formula (I) other than those of formula (Ia): (i), (ii), (iii), (iv), and (v), the disorder or condition may preferably be selected from neurodegenerative disorders, viral or bacterial infections, and metabolic disorders, and is preferably neurodegenerative disorders.

The pharmaceutical compositions of the invention may be administered in any suitably effective manner, for example orally in any orally acceptable dosage form including, but not limited to tablets, dragees, powders, elixirs, syrups, liquid preparations including suspensions, sprays, inhalants, tablets, lozenges, emulsions, solutions, cachets, granules and capsules. Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The magnitude of an effective dose of a compound will, of course, vary with the nature of the severity of the condition to be treated and the route of administration. The selection of appropriate dosages is within the remit of the physician. The daily dose range is about 10 µg to about 100 mg per kg body weight of a human and non-human animal and in general may be around 10 µg to 30 mg per kg body weight per dose. The above dose may be given from one to three times per day.

According to a further aspect, the present invention provides a process for the preparation of a compound of formula (Ia): (i), (ii), (iii), (iv), and (v), according to the second aspect of the invention comprising reacting a compound of formula (IV) with an amine of formula (V), where PG is a protecting group, such as BOC or CBZ, to give a sulfonamide of formula (IIIa).

Additionally, one compound of formula (IIIa) may be converted into another compound of formula (IIIa), for example via a Suzuki coupling of a bromo-aryl or bromo-heteroaryl group.

Sulfonamide (IIIa) may be deprotected using standard methods to give amine (IIa), which may then be reacted with cyanogen bromide to give the compound of formula (Ia).

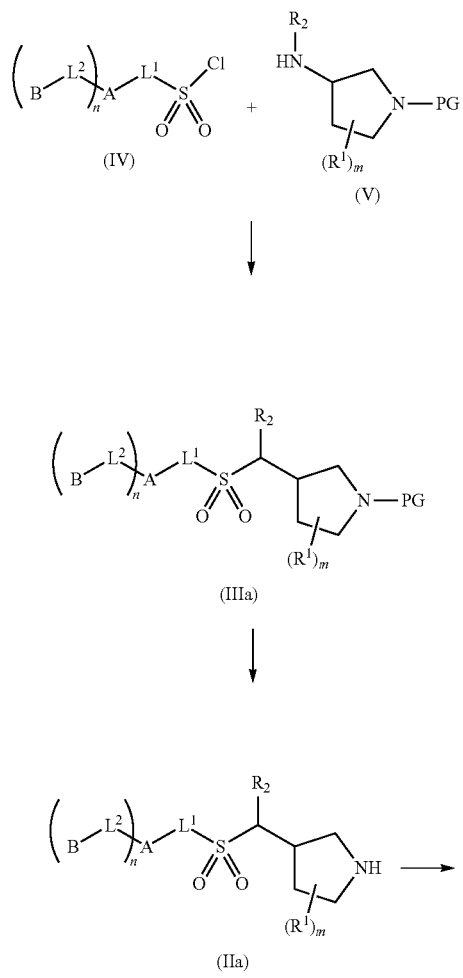

According to a further aspect, the present invention provides an intermediate of formula (IIa) or (IIIa) wherein PG is a protecting group, preferably BOC or CBZ, and m, n, $R^1$, $R^2$, $L^1$, $L^2$, group 'A' and group 'B' are as defined herein for the compound of formula (Ia): (i), (ii), (iii), (iv), and (v), a tautomer thereof, or a salt of said compound or tautomer.

According to a further aspect, the present invention provides a process for the preparation of a compound of formula (Ib) according to the third aspect of the invention comprising reacting an amine of formula (VI), with a compound of formula (VII) where PG is a protecting group, such as BOC or CBZ, to give a sulfonamide of formula (IIIb).

Additionally, one compound of formula (IIIb) may be converted into another compound of formula (IIIb), for example via a Suzuki coupling of a bromo-aryl or bromo-heteroaryl group.

Sulfonamide (IIIb) may be deprotected using standard methods to give amine (IIb), which may then be reacted with cyanogen bromide to give the compound of formula (Ib).

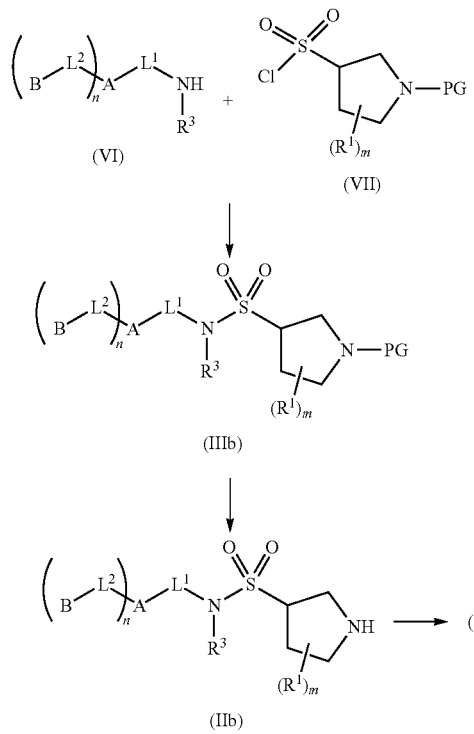

According to a further aspect, the present invention provides an intermediate of formula (IIb) or (ab) wherein PG is a protecting group, preferably BOC or CBZ, and m, n, $R^1$, $R^3$, $L^1$, $L^2$, group 'A' and group 'B' are as defined herein for the compound of formula (Ib), a tautomer thereof, or a salt of said compound or tautomer.

Pharmaceutical acceptable salts of the compounds of formula (I) include the acid addition and base salts (including di-salts) thereof.

Suitable acid addition salts are formed from acids which form non-toxic salts.

Examples include the acetate, aspartate, benzoate, besylate, bicarbonate/carbonate, bisulfate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulfate, 2-napsylate, nicotinate, nitrate, orotate, palmate, phosphate, saccharate, stearate, succinate sulfate, D- and L-tartrate, and tosylate salts.

Suitable base salts are formed from bases which form non-toxic salts. Examples include the aluminium, ammonium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutical acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutical acceptable solvates in accordance with the invention include hydrates and solvates wherein the solvent of crystallization may be isotopically substituted, e.g. $D_2O$, acetone-$d_6$, DMSO-$d_6$.

Also within the scope of the invention are clathrates, drug-host inclusion complexes wherein, in contrast to the aforementioned solvates, the drug and host are present in non-stoichiometric amounts. For a review of such complexes, see J. Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also, within the scope of the invention are so-called "prodrugs" of the compounds of formula (I). Thus, certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Certain derivatives of compounds of formula (I) which contain a nitrogen atom may also form the corresponding N-oxide, and such compounds are also within the scope of the present invention.

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula, including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulphur, such as $^{35}S$, fluorine, such as $^{18}F$, and chlorine, such as $^{36}Cl$.

Substitution of the compounds of the invention with isotopes such as deuterium may afford certain therapeutic advantages resulting from greater metabolic stability, for example, increased in vivo half-life or reduced dosage requirements, and hence may be preferred in some circumstances.

Certain isotopic variations of the compounds of formula (I), for example, those incorporating a radioactive isotope, are useful in drug and/or substrate tissue distribution studies. The radioactive isotopes tritium, and $^{14}C$, are particularly useful for this purpose in view of their ease of incorporation and ready means of detection.

Isotopic variations of the compounds of formula (I) can generally be prepared by conventional techniques known to those skilled in the art or by processes analogous to those described in the accompanying Examples and Preparations using appropriate isotopic variations of suitable reagents.

Synthetic Methodologies

Compounds of formula (I) may be prepared by the skilled person using common general knowledge and the procedures described in WO 01/77073, WO 2009/026197, WO 2009/129365, WO 2009/129370, and WO 2009/129371.

Compounds of formula (I) may also be prepared as described below. Where appropriate, the individual transformations within a scheme may be completed in a different order. The following schemes describe general synthetic methods whereby intermediate and target compounds of the present invention may be prepared. Additional representative compounds and stereoisomers, racemic mixtures, diastereomers and enantiomers thereof may be synthesized using the intermediates prepared in accordance to the general schemes and other materials, compounds and reagents known to those skilled in the art. Enantiomers may be separated using standard techniques, such as Chiral HPLC, for example, using column CHIRALART SA 250×4.6 mm 5 μm.

All the compounds were characterised by liquid chromatography-mass spectroscopy (LCMS) or $^1H$ NMR or both.

Abbreviations

BOC Tert-butyloxycarbonyl
CAS Chemical Abstracts Service
d Doublet (NMR signal)
DCM Dichloromethane
DIPEA Diisopropylethylamine
DMA Dimethylacetamide
DMF N,N-Dimethylformamide
DMSO Dimethyl sulfoxide
dppf 1,1'-Bis(diphenylphosphino)ferrocene
EDC 1-Ethyl-3-(3-dimethylaminopropyl)carbodiimide
ES Electrospray
EtOAc Ethyl acetate
Fmoc Fluorenylmethyloxycarbonyl
Fmoc-OSu 9-Fluorenylmethyl N-succinimidyl carbonate
h Hour(s)
HATU 1-[Bis(dimethylamino)methylene]-1H-1,2,3-triazolo[4,5-b]pyridinium 3-oxide hexafluorophosphate
HOBt 1-Hydroxybenzotriazole
HPLC High performance liquid chromatography
IPA Isopropyl alcohol
LCMS Liquid chromatography mass spectrum
m Multiplet (NMR signal)
MeCN Acetonitrile
MS Mass Spectrum
min Minute(s)
rt Room temperature RT Retention time
s Singlet (NMR signal)
SFC Supercritical fluid chromatography
T3P 2,4,6-Tripropyl-1,3,5,2,4,6-trioxatriphosphorinane-2,4,6-trioxide
TEA Triethylamine
TFA Trifluoroacetic acid
THF Tetrahydrofuran
w/v weight per volume
Analytical Methods LCMS

Method A

| Column | X-bridge C18, 50 × 4.6 mm, 3.5 μm or equivalent |
|---|---|
| Mobile Phase | (A) 0.1% Ammonia in water |
| | (B) 0.1% Ammonia in MeCN |
| Flow Rate | 1.0 ml/min |

| | Time | % B |
|---|---|---|
| Gradient | 0.01 | 5 |
| | 5.00 | 90 |
| | 5.80 | 95 |
| | 7.20 | 95 |

Method B

| Column | BEH C18, 50 × 2.1 mm, 1.7 μm or equivalent |
|---|---|
| Mobile Phase | (A) 5 mM Ammonium acetate + 0.1% formic acid in water |
| | (B) 0.1% Formic acid in MeCN |
| Flow Rate | 0.45 ml/min |

| | Time | % B |
|---|---|---|
| Gradient | 0.01 | 2 |
| | 0.50 | 2 |
| | 5.00 | 90 |
| | 6.00 | 95 |
| | 7.00 | 95 |

Method C

| Column | BEH C18, 50 × 2.1 mm, 1.7 μm or equivalent |
|---|---|
| Mobile Phase | (A) 5 mM Ammonium acetate + 0.1% formic acid in water |
| | (B) 0.1% Formic acid in MeCN |
| Flow Rate | 0.55 ml/min |

| | Time | % B |
|---|---|---|
| Gradient | 0.01 | 5 |
| | 0.40 | 5 |
| | 0.80 | 35 |
| | 1.20 | 55 |
| | 2.50 | 100 |
| | 3.30 | 100 |

Method D

| Column | Agilent TC-C18, 50 × 2.1 mm, 5 μm |
|---|---|
| Mobile Phase | (A) 0.04% TFA in water |
| | (B) 0.02% TFA in MeCN |
| Flow Rate | 0.8 ml/min |

Method D (continued)

| | Time | % B |
|---|---|---|
| Gradient | 0 | 0 |
| | 0.4 | 1 |
| | 3.4 | 100 |
| | 4 | 100 |
| Temperature | 50° C. | |

Method E

| Column | XBridge Shield RP18, 50 × 2.1 mm, 5 μm |
|---|---|
| Mobile Phase | (A) 0.05% Ammonia in water |
| | (B) MeCN |
| Flow Rate | 0.8 ml/min |

| | Time | % B |
|---|---|---|
| Gradient | 0 | 0 |
| | 0.4 | 5 |
| | 3.4 | 100 |
| | 4 | 100 |
| Temperature | 40° C. | |

Method F

| Mobile Phase | (A) 5 mM Ammonium Acetate + 0.1% Formic Acid in Water |
|---|---|
| | (B) 0.1% Formic Acid in Acetonitrile |
| Column | BEH C18 (50*2.1 mm), 1.7 um or Equivalent |
| Flow rate | 0.4 ml/min |

| | Time (min) | % A | % B |
|---|---|---|---|
| Gradient | 0.01 | 90 | 10 |
| | 5.00 | 10 | 90 |
| | 7.00 | 0 | 100 |
| | 11.00 | 0 | 100 |
| | 11.01 | 90 | 10 |
| | 12.00 | 90 | 10 |

General Method A

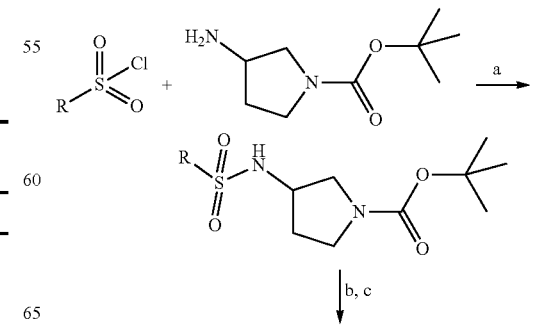

-continued

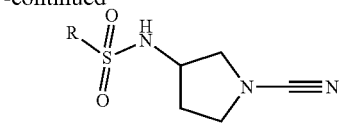

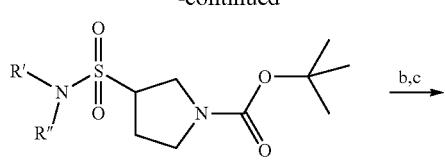

a. Triethylamine, DCM, 0° C. - rt, 48 h; b. TFA, DCM or 6N HCl, MeOH, 100° C., 16 h; c. CNBr, NaHCO₃, DMF, 0° C. - rt, 2 h General Method B

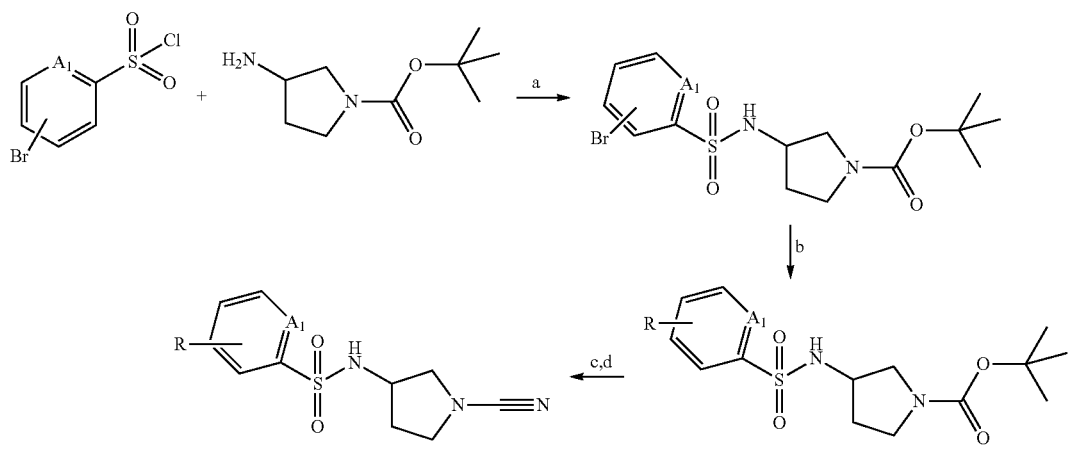

A₁ = C or N a. Triethylamine, DCM, rt, 30 min; b. RB(OH)₂, PdCl₂(PPh₃)₂, NaCO₃, DMF, 100° C., 3 h or R (amine), NaOtBu, Pd₂dba₃, 2-(dicyclohexyl phosphino) biphenyl, toluene, 80° C., 2 h; c. TFA, DCM, rt, 2 h; d. CNBr, K₂CO₃, THF, rt, 1 h.

General Method C

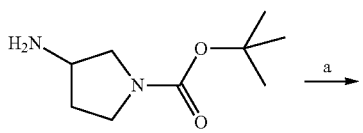

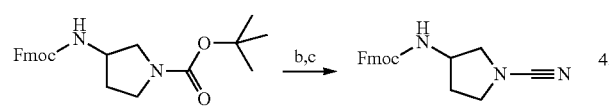

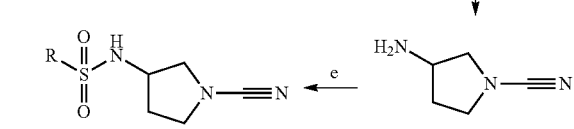

Fmoc—OSu; b. HCl, Dioxane; c. CNBr, NaHCO₃; d. piperidine; e. RSO₂Cl, diethylamine, DCM.

General Method D

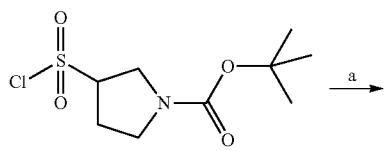

-continued

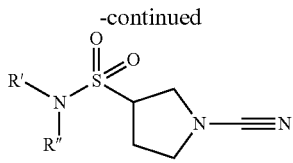

a. R'R''NH, triethylamine, DCM; b. TFA, DCM; c. CNBr, NaHCO₃.

Compounds in Table 1 were synthesised according to General Method A.

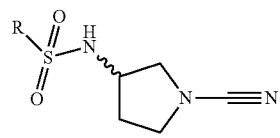

TABLE 1

| Ex | R | Name | ¹H NMR: (400 MHz, DMSO-d₆) δ ppm | LCMS method | LCMS RT (min) | MS (ES+) |
|---|---|---|---|---|---|---|
| 1 | | N-(1-cyanopyrrolidin-3-yl)-[1,1'-biphenyl]-2-sulfonamide | 7.99 (dd, J = 1.2, 8 Hz, , 1 H), 7.77 (d, J = 6.8 Hz, 1H), 7.62-7.72 (m, 1 H), 7.50-7.61 (m, 1 H), 7.32-7.48 (m, 5 H), 3.46-3.52 (m, 1 H), 3.33-3.40 (m, 1 H), 3.26-3.31 (m, 2 H), 3.00-3.03 (m, 1 H), 1.81-1.90 (m, 1 H), 1.64-1.72 (m, 1 H) | A | 4.260 | 327.95 |
| 2 | | N-(1-cyanopyrrolidin-3-yl)-[1,1'-biphenyl]-4-sulfonamide | 8.16 (d, J = 6.4 Hz, 1 H), 7.89-7.93 (m, 4 H), 7.75-7.77 (m, 2 H), 7.52 (t, J = 7.2 Hz, 2 H), 7.45 (t, J = 7.2 Hz, 1 H), 3.73-3.77 (m, 1 H), 3.39-3.45 (m, 2 H), 3.31-3.36 (m, 1 H), 3.13 (dd, J = 4.4 Hz & 10.0 Hz, 1 H), 1.86-1.95 (m, 1 H), 1.69-1.760 (m, 1 H) | A | 4.276 | 327.95 |
| 3 | | (R)-N-(1-cyanopyrrolidin-3-yl)-[1,1'-biphenyl]-4-sulfonamide | 8.15-8.17 (d, J = 6.4 Hz, 1 H), 7.89-7.94 (m, 4 H), 7.75-7.77 (m, 2 H), 7.52 (t, J = 6.8 Hz, 2 H), 7.45 (t, J = 7.2 Hz, 1 H), 3.72-3.77 (m, 1H), 3.31-3.45 (m, 3 H), 3.10-3.14 (m, 1 H), 1.86-1.93 (m, 1 H), 1.69-1.75 (m, 1 H) | A | 4.271 | 327.95 |
| 4 | | (S)-N-(1-cyanopyrrolidin-3-yl)-[1,1'-biphenyl]-4-sulfonamide | 8.15-8.17 (d, J = 6.0 Hz, 1 H), 7.89-7.94 (m, 4 H), 7.75-7.77 (m, 2 H), 7.51-7.54 (m, 2 H), 7.43-7.47 (m, 1 H), 3.72-3.77 (m, 1 H), 3.31-3.45 (m, 3 H), 3.10-3.18 (m, 1 H), 1.86-1.93 (m, 1 H), 1.69-1.74 (m, 1 H) | A | 4.270 | 327.95 |
| 5 | | N-(1-cyanopyrrolidin-3-yl)benzenesulfonamide | 8.11-8.12 (d, J = 6.4 Hz, 1 H), 7.82-7.84 (m, 2 H), 7.60-7.70 (m, 3 H), 3.68-3.73 (m, 1 H), 3.29-3.43 (m, 3 H), 3.04-3.07 (dd, J = 4.4 Hz & 9.6 Hz, 1 H), 1.82-1.90 (m, 1 H), 1.62-1.70 (m, 1 H) | F | 2.359 | 252.13 |
| 6 | | (S)-N-(1-cyanopyrrolidin-3-yl)benzenesulfonamide | 8.12 (d, J = 6.4 Hz, 1 H), 7.84-7.82 (m, 2 H), 7.70-7.60 (m, 3 H), 3.73-3.67 (m, 1 H), 3.43-3.29 (m, 3 H), 3.08-3.04 (m, 1 H), 1.90-1.82 (m, 1 H), 1.70-1.62 (m, 1 H) | B | 3.011 | 253.17 |
| 7 | | (R)-N-(1-cyanopyrrolidin-3-yl)benzenesulfonamide | 8.12 (d, J = 6.4 Hz, 1 H), 7.84-7.82 (m, 2 H), 7.70-7.60 (m, 3 H), 3.73-3.67 (m, 1 H), 3.43-3.29 (m, 3 H), 3.08-3.04 (m, 1 H), 1.90-1.82 (m, 1 H), 1.70-1.62 (m, 1 H) | B | 3.013 | 253.17 |
| 8 | | (4-(benzyloxy)-N-(1-cyanopyrrolidin-3-yl)benzenesulfonamide | 7.91 (d, J = 6.4 Hz, 1 H), 7.76-7.73 (m, 2 H), 7.48-7.46 (m, 2 H), 7.43-7.41 (m, 2 H), 7.37-7.34 (m, 1 H), 7.21 (dd, J = 6.8, 1.6 Hz, 2 H), 5.20 (s, 2 H), 3.68-3.64 (m, 1 H), 3.42-3.36 (m, 2 H), 3.31-3.28 (m, 1 H), 3.06 (dd, J = 9.6, 4.4 Hz, 1 H), 1.88-1.83 (m, 1 H), 1.70-1.64 (m, 1 H) | A | 4.425 | 357.89 |

Compounds in Table 2 were synthesised according to general method B.

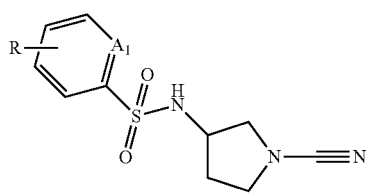

TABLE 2

| Ex | R-A₁ structure | Name | ¹H NMR: (400 MHz, DMSO-d₆) δ ppm | LCMS Method | LCMS RT (min) | MS |
|---|---|---|---|---|---|---|
| 9 | pyrimidin-5-yl | N-(1-cyanopyrrolidin-3-yl)-4-(pyrimidin-5-yl)benzenesulfonamide | 9.24-9.30 (m, 3 H), 8.25 (d, J = 6 Hz, 1 H), 8.08 (d, J = 8.4 Hz, 2 H), 7.96 (d, J = 8.4 Hz, 2 H), 3.74-3.78 (m, 1 H), 3.39-3.45 (m, 2 H), 3.31-3.33 (m, 1 H), 3.11-3.14 (m, 1 H), 1.86-1.93 (m, 1 H), 1.69-1.75 (m, 1 H) | B | 2.828 | 330.23 |
| 10 | 4-methylpiperazin-1-yl phenyl | N-(1-cyanopyrrolidin-3-yl)-4-(4-methylpiperazin-1-yl)benzenesulfonamide | 7.74 (d, J = 6 Hz, 1 H), 7.59 (d, J = 8.8 Hz, 2 H), 7.059 (d, J = 9.2 Hz, 2 H), 3.58-3.62 (m, 1 H), 3.29-3.42 (m, 7 H), 3.05-3.08 (m, 1 H), 2.42-2.45 (m, 4 H), 2.22 (s, 3 H), 1.81-1.87 (m, 1 H), 1.65-1.71 (m, 1 H) | B | 2.155 | 350.43 |
| 11 | 5-phenylpyridin-2-yl | N-(1-cyanopyrrolidin-3-yl)-5-phenylpyridine-2-sulfonamide | 9.08-9.08 (m, 1 H), 8.37-8.41 (m, 2 H), 8.02-8.04 (d, J = 8.0 Hz, 1 H), 7.83-7.85 (d, J = 7.2 Hz, 2 H), 7.48-7.64 (m, 3 H), 3.98-4.02 (q, 1 H), 3.34-3.48 (m, 3 H), 3.16-3.21 (m, 1 H), 1.93-2.01 (m, 1 H), 1.77-1.83 (m, 1 H) | A | 3.792 | 328.94 |
| 12 | 4'-fluorobiphenyl | N-(1-cyanopyrrolidin-3-yl)-4'-fluoro-[1,1'-biphenyl]-4-sulfonamide | 8.16 (d, J = 6 Hz, 1 H), 7.87-7.92 (m, 4 H), 7.80-7.84 (m, 2 H), 7.33-7.38 (m, 2 H), 3.72-3.76 (m, 1 H), 3.39-3.44 (m, 2 H), 3.30-3.36 (m, 1 H), 3.10-3.13 (m, 1 H), 1.88-1.92 (m, 1 H), 1.68-1.73 (m, 1 H) | B | 4.103 | 346.28 |
| 13 | pyridin-4-yl phenyl | N-(1-cyanopyrrolidin-3-yl)-4-(pyridin-4-yl)benzenesulfonamide | 8.70 (dd, J = 4.4 Mz, 4.4 Hz, 2H), 8.24 (d, J = 6 Hz, 1 H), 8.05-8.07 (m, 2 H), 7.94-8.01 (m, 2 H), 7.80 (dd, J = 4.4 Hz & 4.8 Hz, 2H), 3.74-3.78 (m, 1 H), 3.42-3.45 (m, 2 H), 3.30-3.36 (m, 1 H), 3.10-3.13 (m, 1 H), 1.86-1.95 (m, 1 H), 1.68-1.75 (m, 1 H) | B | 2.506 | 329.21 |
| 14 | piperidin-1-yl phenyl | N-(1-cyanopyrrolidin-3-yl)-4-(piperidin-1-yl)benzenesulfonamide | 7.67 (dd, J = 7.2 Hz, 2 H), 7.03 (m, 3 H), 3.75-3.77 (m, 1 H), 3.37-3.51 (m, 7 H), 3.14-3.18 (m, 1 H), 1.98-2.03 (m, 1 H), 1.77-1.85 (m, 1 H), 1.60-1.76 (m, 6 H) | B | 3.935 | 335.28 |
| 15 | 1-methyl-1H-pyrazol-4-yl | N-(1-cyanopyrrolidin-3-yl)-4-(1-methyl-1H-pyrazol-4-yl)benzenesulfonamide | 8.30 (s, 1 H), 8.045 (d, J = 6.4 Hz, 1 H), 8.00 (s, 1 H), 7.76-7.81 (m, 4 H), 3.88 (s, 3 H), 3.68-3.73 (m, 1 H), 3.29-3.43 (m, 3 H), 3.06-3.10 (m, 1 H), 1.83-1.91 (m, 1 H), 1.65-1.72 (s, 1 H) | B | 3.149 | 332.33 |

Compounds in Table 3 were synthesised according to general method C.

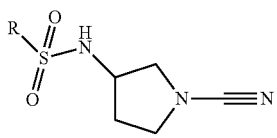

TABLE 3

| Ex | R | Name | LCMS Method | LCMS RT (min) | MS |
|----|---|------|-------------|---------------|-----|
| 16 | | N-(1-cyanopyrrolidin-3-yl)-6-phenoxypyridine-3-sulfonamide | D | 2.591 | 345.1 |
| 17 | | N-(1-cyanopyrrolidin-3-yl)-5-fluoro-2-methylbenzenesulfonamide | E | 2.047 | 284.2 |
| 18 | | N-(1-cyanopyrrolidin-3-yl)-4-isopropylbenzenesulfonamide | E | 2.492 | 294.2 |
| 19 | | N-(1-cyanopyrrolidin-3-yl)-4-((5-(trifluoromethyl)pyridin-2-yl)oxy)benzenesulfonamide | D | 2.817 | 413.2 |

EXAMPLE 20

(R)—N-(1-cyanopyrrolidin-3-yl)-N-methyl-4-(pyridin-3-yl)benzenesulfonamide

Step 1. tert-Butyl (R)-3-((4-bromo-N-methylphenyl)sulfonamido) pyrrolidine-1-carboxylate)

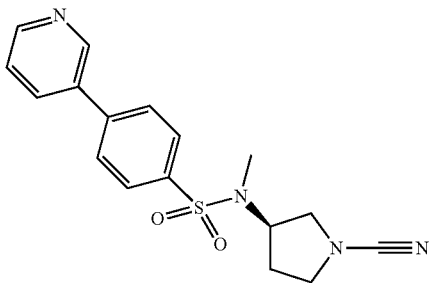 [SMILES: CN([C@@H]1CCN(C#N)C1)S(=O)(=O)c1ccc(-c2cccnc2)cc1]

To a stirred solution of tert-butyl (R)-3-(methylamino) pyrrolidine-1-carboxylate (CAS no. 199336-83-9, Available from Combi Blocks) (0.500 g, 2.50 mmol) in THF was added TEA (0.756 g, 7.49 mmol) at 0° C. under nitrogen and stirred for 10 min at the same temperature. A solution of 4-bromobenzenesulfonyl chloride (CAS No. 98-58-8, available from Combi-blocks) (0.636 g, 2.50 mmol) in THF (1 mL) was slowly added to the reaction mixture at 0° C. The reaction mixture was stirred for 1 h at room temperature. The resulting reaction mixture was diluted with water (30 mL) and was extracted with EtOAc (3×20 mL). The combined organic phases were dried over anhydrous Na$_2$SO$_4$, filtered and concentrated under reduced pressure to yield tert-butyl (R)-3-((4-bromo-N-methylphenyl)sulfonamido)-pyrrolidine-1-carboxylate [1.00 g, 95.5% (crude)]. LCMS: Method C, 2.427 min, MS: ES+363.1, 365.1 (M−56).

Step 2. tert-Butyl (R)-3-((N-methyl-4-(pyridin-3-yl)phenyl)sulfonamido)pyrrolidine-1-carboxylate

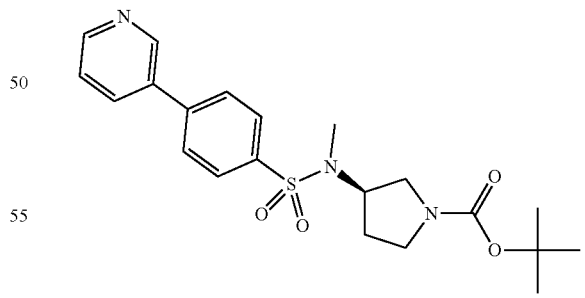

To a mixture of tert-butyl (R)-3-((4-bromo-N-methylphenyl)sulfonamido)pyrrolidine-1-carboxylate (1.0 g, 2.39 mmol) and pyridine-3-boronic acid (CAS No. 1692-25-7, available from Combi-blocks) (0.293 g, 2.39 mmol) in DMF-water (3:2; 5 mL) was added Na$_2$CO$_3$ (0.505 g, 4.77 mmol). Resulting mixture was degassed (by purging nitrogen through the reaction solution) for 15 to 20 min. Tetrakis(triphenylphosphine)palladium (O) (0.275 g, 0.24 mmol)

was added into the reaction solution and the resulting mixture was stirred at 110° C. for 16 h. The reaction mixture was cooled to room temperature and diluted with water (110 mL) and was extracted with EtOAc (3×50 mL). The combined organic extracts were dried over anhydrous Na₂SO₄, filtered and concentrated under reduced pressure to yield tert-butyl (R)-3-((N-methyl-4-(pyridin-3-yl)phenyl)sulfonamido)pyrrolidine-1-carboxylate (0.5 g, 1.199 mmol) as crude mass. LCMS: Method C, 2.035 min, MS: ES+418.3.

Step 3. (R)—N-methyl-4-(pyridin-3-yl)-N-(pyrrolidin-3-yl)benzenesulfonamide TFA salt

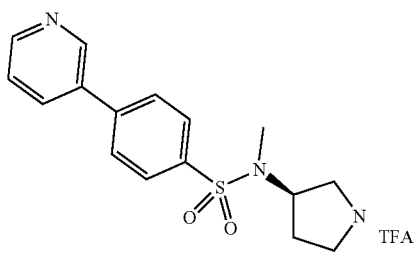 [SMILES: CN([C@@H]1CCNC1)S(=O)(=O)c1ccc(-c2cccnc2)cc1]

To a solution of (R)-3-((N-methyl-4-(pyridin-3-yl)phenyl)sulfonamido)pyrrolidine-1-carboxylate (0.4 g, 0.96 mmol) in DCM (5 mL) was added TFA (1 mL) at 0° C. and the resulting solution was stirred at room temperature for 4 h. Reaction mixture was concentrated under reduced pressure. The crude was azeotropically distilled with diethyl ether (2×10 mL) and dried under reduced pressure to afford (R)—N-methyl-4-(pyridin-3-yl)-N-(pyrrolidin-3-yl)benzenesulfonamide TFA salt (0.4 g, quantitative). LCMS: Method C, 1.377 min, MS: ES+318.3.

Step 4. (R)—N-(1-cyanopyrrolidin-3-yl)-N-methyl-4-(pyridin-3-yl)-benzenesulfonamide To a stirred solution (R)—N-methyl-4-(pyridin-3-yl)-N-(pyrrolidin-3-yl)-benzenesulfonamide TFA salt (0.400 g, 0.93 mmol) in THF (5 mL) was added K₂CO₃ (0.384 g, 2.78 mmol) at 0° C. CNBr (0.118 g, 1.11 mmol) was added into the reaction mixture at 0° C. The reaction mixture was stirred at room temperature for 1 h. The resulting reaction mixture was poured in to water (50 mL) and was extracted with EtOAc (3×50 mL). Combined organic extracts were dried over Na₂SO₄, filtered and concentrated under reduced pressure. The resulting residue was purified by Combi-flash Column chromatography (silica; eluted with 2.5% MeOH in DCM) yielding title compound (0.080 g, 0.23 mmol). LCMS: Method B, 3.096 min, MS: ES+343.1 [M+1]; ¹H NMR (400 MHz, CDCl3) δ ppm: 9.00 (d, J=2 Hz, 1H), 8.66 (dd, J=4.8, 1.2 Hz, 1H), 8.19 (dt, J=8.0, 1.6 Hz, 1H), 8.01 (d, J=8.8 Hz, 2H), 7.93 (d, J=8.4 Hz, 2H), 7.57-7.54 (m, 1H), 4.64-4.60 (m, 1H), 3.45-3.40 (m, 2H), 3.33-3.29 (m, 1H), 3.20-3.15 (m, 1H), 2.72 (s, 3H), 1.88-1.83 (m, 1H), 1.79-1.73 (m, 1H).

EXAMPLE 21

(3aR,6aR)-1-((4-(pyridin-3-yl)phenyl)sulfonyl)hexahydropyrrolo[3,4-b]pyrrole-5(1H)-carbonitrile

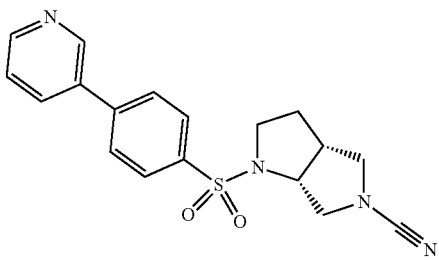 [SMILES: N#CN1C[C@H]2CCN(S(=O)(=O)c3ccc(-c4cccnc4)cc3)[C@H]2C1]

Step 1. tert-butyl rac-(3aR,6aR)-1-((4-bromophenyl)sulfonyl)hexahydropyrrolo-[3,4-b]pyrrole-5(1H)-carboxylate

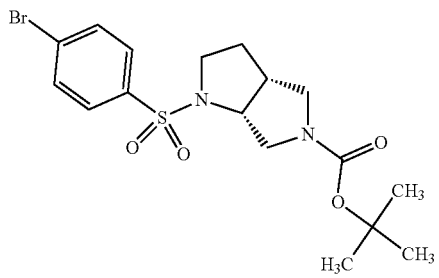 [SMILES: CC(C)(C)OC(=O)N1C[C@H]2CCN(S(=O)(=O)c3ccc(Br)cc3)[C@H]2C1]

To a stirred solution of 4-bromobenzene sulfonyl chloride (CAS No. 98-58-8, available from Alfa Aesar) (0.2 g, 0.78 mmol) and tert-butyl rac-(3aS,6aS)-hexahydropyrrolo[3,4-b]pyrrole-5(1H)-carboxylate (CAS No. 180975-51-3, available from Enamine) (0.166 g, 0.78 mmol) in THF (10 mL) was added K₂CO₃ (0.324 g, 2.35 mmol) at ambient temperature. The reaction mixture was stirred at room temperature for 8 h. The resulting reaction mixture was diluted with water (200 mL) and was extracted with diethyl ether (3×100 mL).

Combined organic extracts were dried over anhydrous Na₂SO₄, filtered and concentrated under reduced pressure to yield tert-butyl rac-(3aR,6aR)-1-((4-bromophenyl)sulfonyl)hexahydropyrrolo[3,4-b]pyrrole-5(1H)-carboxylate (0.350 g, Quantitative) as crude mass. LCMS: Method C, 2.667 min, MS: ES+448.3, 450.3 (M+18).

Step 2. tert-butyl (3aR,6aR)-1-((4-(pyridin-3-yl)phenyl)sulfonyl)hexahydropyrrolo-[3,4-b]pyrrole-5(1H)-carboxylate

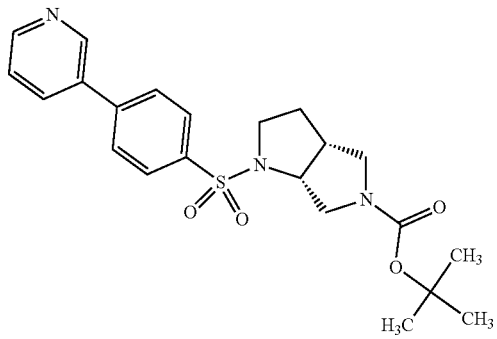 [SMILES: CC(C)(C)OC(=O)N1C[C@H]2CCN(S(=O)(=O)c3ccc(-c4cccnc4)cc3)[C@H]2C1]

To a mixture of tert-butyl rac-(3aR,6aR)-1-((4-bromophenyl)sulfonyl)-hexahydropyrrolo[3,4-b]pyrrole-5(1H)-carboxylate (0.350 g, 0.81 mmol), pyridine-3-boronic acid (CAS No. 1692-25-7, available from Combiblocks) (0.120 g, 0.98 mmol) and in DMF-water (4:1; 17.5 mL) was added K$_2$CO$_3$ (0.224 g, 1.62 mmol). The reaction mixture was degassed (by purging nitrogen through the solution) for 30 min. PdCl$_2$(dppf) (0.060 g, 0.08 mmol) was added into the reaction mixture and the resulting mixture was stirred at 80° C. for 2 h. Reaction mixture was cooled to room temperature, diluted with saturated aqueous NaHCO$_3$ (350 mL) and was extracted with EtOAc (3×200 mL). The combined organic phase was dried over Na$_2$SO$_4$, filtered and concentrated under reduced pressure. The resulting residue was purified by Flash column chromatography (eluting with 3% MeOH in DCM) to yield tert-butyl rac-(3aR,6aR)-1-((4-(pyridin-3-yl)phenyl)sulfonyl)hexa-hydropyrrolo[3,4-b]pyrrole-5(1H)-carboxylate (0.350 g, 0.82 mmol). LCMS: Method C, 2.160 min, MS: ES+430.5

Step 3. rac-(3aR,6aR)-1-((4-(pyridin-3-yl)phenyl)sulfonyl)octahydropyrrolo[3,4-b]pyrrole TFA salt

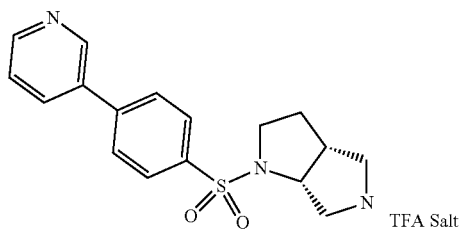 [SMILES: O=S(=O)(c1ccc(-c2cccnc2)cc1)N1CC[C@@H]2CNC[C@@H]21]

To a stirred solution of tert-butyl rac-(3aR,6aR)-1-((4-(pyridin-3-yl)phenyl)sulfonyl)hexahydropyrrolo[3,4-b]pyrrole-5(1H)-carboxylate (0.350 g, 0.82 mmol) in DCM (20 mL) was added TFA (2 mL) at 0° C. The reaction mixture was stirred at room temperature for 2 h. The reaction mixture was concentrated under reduced pressure. The crude residue was further azetropically distilled with diethyl ether (3×10 mL) and dried under reduced pressure to afford rac-(3aR, 6aR)-1-((4-(pyridin-3-yl)phenyl)sulfonyl) octahydropyrrolo[3,4-b]pyrrole TFA salt (0.210 g, quantitative) as crude mass. LCMS: Method C, 1.472 min, MS: ES+330.29

Step 4. (3aR,6aR)-1-((4-(pyridin-3-yl)phenyl)sulfonyl)hexahydropyrrolo[3,4-b]pyrrole-5(1H)-carbonitrile

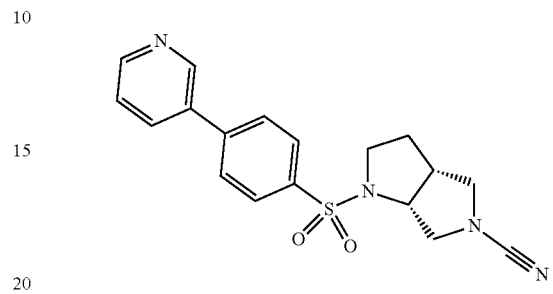

To a stirred solution rac-(3aR,6aR)-1-((4-(pyridin-3-yl)phenyl)sulfonyl) octahydropyrrolo[3,4-b]pyrrole TFA salt (0.200 g, 0.45 mmol) in THF (20 mL) was added K$_2$CO$_3$ (0.333 g, 2.41 mmol) at 0° C. followed by the addition of CNBr (0.051 g, 0.48 mmol) at the same temperature. The reaction mixture was stirred at room temperature for 1 h. The resulting reaction mixture was concentrated under reduced pressure and resulting residue was purified by flash column chromatography (eluting with 3.0% MeOH in DCM) yielding the title compound (0.150 g, 0.423 mmol). LCMS: Method A, 3.698 min, MS: ES+354.9 [M+1]; $^1$H NMR (400 MHz, DMSO-D6): 8.96 (d, J=2 Hz, 1H), 8.65-8.64 (m, 1H), 8.19-8.17 (m, 1H), 8.02 (d, J, 8.4 Hz, 2H), 7.95 (d, J=8.8 Hz, 2H), 7.54-7.57 (m, 1H), 4.05-4.01 (m, 1H), 3.58 (d, J=7.2 Hz, 2H), 3.56-3.48 (m, 1H), 3.41-3.28 (m, 1H), 3.35 (dd, J=10.0 & 6.0 Hz, 1H), 3.18-3.14 (m, 1H), 1.74-1.62 (m, 1H), 1.65-1.71 (m, 2H).

EXAMPLE 22 rac-(4aR,7aR)-4-tosylhexahydropyrrolo[3,4-b][1,4]oxazine-6(2H)-carbonitrile

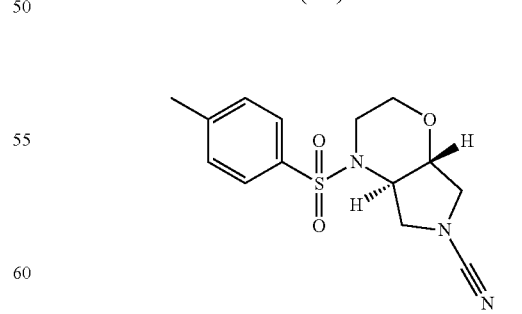

The title compound was synthesised via general method A using pyrrolo[3,4-b]-1,4-oxazine-6(2H)-carboxylic acid, hexahydro-1,1-dimethylethyl ester, (4aR,7aS) in step a. LCMS: Method D, 2.591 min, MS: ES+345.1 [M+1].

EXAMPLE 23 rac-(4aR,7aS)-4-(4-methylbenzyl)sulfonyl)hexahydropyrrolo[3,4-b][1,4]oxazine-6(2H)-carbonitrile

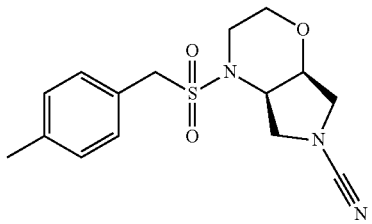 [SMILES: Cc1ccc(CS(=O)(=O)N2CCO[C@H]3CN(C#N)C[C@H]32)cc1]

The title compound was synthesised via general method A using pyrrolo[3,4-b]-1,4-oxazine-6(2H)-carboxylic acid, hexahydro-1,1-dimethylethyl ester, (4aR,7aS) in step a. LCMS: Method D, 2.591 min, MS: ES+322.4 [M+1].

EXAMPLE 24

N-(5-(N-(1-cyanopyrrolidin-3-yl)sulfamoyl)pyridin-2-yl)-1-methyl-1H-pyrazole-5-carboxamide

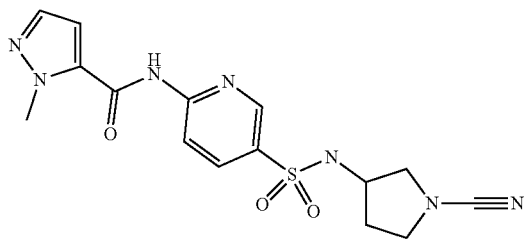 [SMILES: Cn1nccc1C(=O)Nc1ccc(S(=O)(=O)NC2CCN(C#N)C2)cn1]

Step 1. pyridin-2-amine was heated to 150° C. in chlorosulfonic acid to afford 6-aminopyridine-3-sulfonyl chloride which was used crude in the next reaction.

Step 2. 6-aminopyridine-3-sulfonyl chloride was added to tert-butyl 3-aminopyrrolidine-1-carboxylate using general method A, step a to afford t-butyl 3-((6-aminopyridine)-3-sulfonamido)pyrrolidine-1-carboxylate.

Step 3. t-butyl 3-((6-aminopyridine)-3-sulfonamido)pyrrolidine-1-carboxylate and 1-methyl-1H-pyrazole-5-carboxylic acid were heated to 70° C. with 50% T3P in ethyl acetate, triethylamine and THF for 30 h to afford tert-butyl 3-((6-(1-methyl-1H-pyrazole-5-carboxamido)pyridine)-3-sulfonamido)pyrrolidine-1-carboxylate.

Step 4. The title compound was synthesised following the procedure of general method A, steps b-c. LCMS: Method B, 2.998 min, MS: ES+376.13 [M+1]; $^1$H NMR (400 MHz, DMSO-d6) δ 11.32 (s, 1H), 8.77 (d, J=2.4 Hz, 1H), 8.37 (d, J=8.4 Hz, 1H), 8.24-8.26 (m, 2H), 7.55 (d, J=2 Hz, 1H), 7.34 (d, J=2 Hz, 1H), 4.1 (s, 3H), 3.78-3.82 (m, 1H), 3.31-3.46 (m, 3H), 3.09-3.12 (m, 1H), 1.88-1.99 (m, 1H), 1.66-1.74 (m, 1H).

EXAMPLE 25

N-(1-cyanopyrrolidin-3-yl)-N-methyl-4-((5-(trifluoromethyl)pyridin-2-yl)oxy)benzenesulfonamide

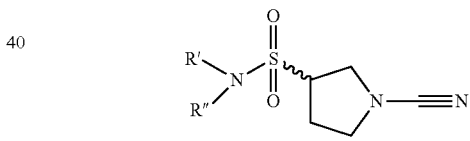

The title compound was synthesised via general method C using tert-butyl 3-(methylamino)pyrrolidine-1-carboxylate in step a. LCMS: Method D, 3.046 min, MS: ES+427.2 [M+1].

Compounds in Table 4 were synthesised according to General Method D.

TABLE 4

| Ex | R'R"N— | Name | LCMS Method | LCMS RT (min) | LCMS MS (ES+) |
|----|--------|------|-------------|---------------|---------------|
| 26 | | N-([1,1'-biphenyl]-4-yl)-1-cyanopyrrolidine-3-sulfonamide | B | 4.193 | 326.2 (ES−) |
| 27 | | 3-((4-(4-fluorophenyl)piperazin-1-yl)sulfonyl)pyrrolidine-1-carbonitrile | D | 2.603 | 339.1 |

TABLE 4-continued

| Ex | R'R"N— | Name | LCMS Method | LCMS RT (min) | MS (ES+) |
|---|---|---|---|---|---|
| 28 | | (3-((4-(pyridin-2-yl)piperazin-1-yl)sulfonyl)pyrrolidine-1-carbonitrile | E | 2.162 | 322.1 |
| 29 | | 3-((4-(pyrimidin-2-yl)piperazin-1-yl)sulfonyl)pyrrolidine-1-carbonitrile | E | 1.889 | 323.1 |
| 30 | | 3-((4-(4-chlorophenyl)piperidin-1-yl)sulfonyl)pyrrolidine-1-carbonitrile | D | 2.824 | 354.1 |
| 31 | | (S)-3-((4-(4-chlorophenyl)piperidin-1-yl)sulfonyl)pyrrolidine-1-carbonitrile | B | 4.586 | 370.5 |
| 32 | | (R)-3-((4-(4-chlorophenyl)piperidin-1-yl)sulfonyl)pyrrolidine-1-carbonitrile | B | 4.561 | 370.5 |
| 33 | | 3-((4-benzylpiperidin-1-yl)sulfonyl)pyrrolidine-1-carbonitrile | D | 3.107 | 334.2 |
| 34 | | 3-((3-(4-chlorophenyl)azetidin-1-yl)sulfonyl)pyrrolidine-1-carbonitrile | B | 4.129 | 326.3 |
| 35 | | (S)-3-((3-(4-chlorophenyl)azetidin-1-yl)sulfonyl)pyrrolidine-1-carbonitrile | B | 4.211 | 326.3 |
| 36 | | (R)-3-((3-(4-chlorophenyl)azetidin-1-yl)sulfonyl)pyrrolidine-1-carbonitrile | B | 4.220 | 326.3 |
| 37 | | 3-((3-phenoxyazetidin-1-yl)sulfonyl)pyrrolidine-1-carbonitrile | A | 4.239 | 308.0 |

Biological Activity of Compounds of the Invention

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue In Vitro UCHL1 Inhibition Assay
Expression and Purification of UCHL1

The UCHL1 construct was PCR amplified and cloned into a pFLAG-CMV-6a vector (Sigma-Aldrich) with an N-terminal FLAG tag. HEK293T cells were transfected with FLAG-UCHL1 using TransIT-LT1 transfection reagent (Mirus) according to the manufacturer's instructions. Cells were harvested 40 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 1200 rpm for 10 min at 4° C. Soluble supernatant was added to FLAG affinity resin (EZview Rad ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound UCHL1, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3× FLAG peptide (Sigma-Aldrich)) was added to the resin and incubated at 4° C. for 2.5 hours rotating. The resin was centrifuged at 4000 rpm for 30 seconds, and the supernatant containing purified FLAG-UCHL1 was removed and stored at −80° C.

UCHL1 Biochemical Kinetic Assay

Reactions were performed in duplicate in black 384 well plates (small volume, Greiner 784076) in a final reaction volume of 21 µl. UCHL1 was diluted in reaction buffer (20 mM Tris, pH 7.5, 100 mM NaCl, 0.05% Tween 20, 0.5 mg/ml BSA, 5 mM beta-mercaptoethanol) to the equivalent of 0, 0.01, 0.05, 0.1, 0.5, and 1 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

UCHL1 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series to be 30, 10, 3, 1, 0.3, 0.1, 0.03, 0.01 µM final. Reactions were performed in duplicate in black 384 well plates (small volume, Greiner 784076) in a final reaction volume of 21 µl. Either 1 µl of 50% DMSO or diluted compound was added to the plate. UCHL1 was diluted in reaction buffer (20 mM Tris, pH 7.5, 100 mM NaCl, 0.05% Tween 20, 0.5 mg/ml BSA, 5 mM beta-mercaptoethanol) to the equivalent of 0.05 µl/well and 10 µl of diluted UCHL1 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2-hour incubation at room temperature. Readings were performed on a Pherastar Plus (BMG Labtech). λ Excitation 540 nm; λ Emission 590 nm.

Activity of Exemplary Compounds in UCHL1 Biochemical 1050 Assay
Ranges:
A<0.1 µM;
0.1<B<1 µM;
1<C<10 µM;
10 µM<D<100 µM

| Example | IC50 range |
| --- | --- |
| 1 | D |
| 2 | C |
| 3 | D |
| 4 | C |
| 5 | D |
| 6 | D |
| 8 | C |
| 9 | C |
| 11 | D |
| 12 | C |
| 13 | C |
| 14 | D |
| 15 | C |
| 16 | D |
| 18 | D |
| 19 | B |
| 20 | C |
| 24 | D |
| 25 | C |
| 26 | D |

In Vitro USP30 Inhibition Assay

USP30 biochemical kinetic assay. Reactions were performed in duplicate in black 384 well plates (small volume, Greiner 784076) in a final reaction volume of 21 µl. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical 1050 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 µl/well and 10 µl of diluted USP30 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2-hour incubation at room temperature. Readings were performed on a Pherastar Plus (BMG Labtech). λ Excitation 540 nm; λ Emission 590 nm.

Activity of Exemplary Compounds in USP30 Biochemical IC50 Assay
Ranges:
A<0.1 µM;
0.1<B<1 µM;
1<C<10 µM;
10 µM<D<100 µM

| Example | IC50 range |
|---|---|
| 1 | B |
| 2 | B |
| 3 | B |
| 4 | B |
| 6 | C |
| 7 | C |
| 8 | B |
| 9 | B |
| 10 | C |
| 11 | B |
| 13 | B |
| 14 | B |
| 15 | B |
| 16 | B |
| 17 | C |
| 18 | C |
| 19 | B |
| 20 | B |
| 21 | B |
| 22 | D |
| 23 | B |
| 24 | B |
| 25 | B |
| 26 | B |
| 27 | D |
| 28 | B |
| 29 | C |
| 30 | A |
| 31 | A |
| 32 | A |
| 33 | B |
| 34 | B |
| 35 | B |
| 36 | B |
| 37 | D |

The invention claimed is:

1. A compound of formula (Ia):

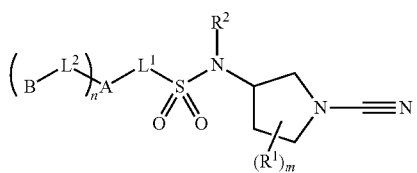

or a tautomer thereof, or a pharmaceutically acceptable salt of said compound or tautomer,
wherein:
m is 1 to 4;
n is 0 or 1;
one $R^1$ group and $NR^2$ are situated on adjacent ring atoms, and said $R^1$ together with $R^2$ forms a pyrrolidine ring;
each other $R^1$ group is independently selected from halo, cyano, hydroxy, $(C_1-C_6)$alkyl, $(C_1-C_6)$alkoxy, halo$(C_1-C_6)$alkyl, halo$(C_1-C_6)$alkoxy, and $(C_1-C_6)$alkoxy$(C_1-C_6)$alkyl;
$L^1$ is selected from a covalent bond, $(C_1-C_4)$alkylene, and $(C_2-C_4)$alkenylene;
$L^2$ is selected from a covalent bond, $(C_1-C_4)$alkylene, $(C_2-C_4)$alkenylene, and $(C_0-C_3)$alkylene-X—$(C_0-C_3)$alkylene;
X is selected from O, S, SO, $SO_2$, $NR^4$, $NR^4C(O)$, $C(O)NR^4$, $NR^4C(O)NR^5$, $C(O)$, $C(O)O$, $OC(O)$, $OC(O)O$, $SO_2NR^4$, $NR^4SO_2$, and $NR^4SO_2NR^5$;
$R^4$ and $R^5$ are each independently selected from hydrogen, $(C_1-C_6)$alkyl, and $(C_1-C_6)$alkoxy$(C_1-C_6)$alkyl;
group 'A' is selected from a 3 to 10-membered carbocyclic ring, and a 3 to 10-membered heterocyclic ring comprising 1 to 4 heteroatoms independently selected from N, O, and S; with the proviso that for the compound of formula (Ia) when $L^1$ is a covalent bond, 'A' is linked to the sulfonamide via a ring C-atom;
group 'B' is selected from a 3 to 10-membered carbocyclic ring, and a 3 to 10-membered heterocyclic ring comprising 1 to 4 heteroatoms independently selected from N, O, and S; and
each carbocyclic and heterocyclic ring may be optionally substituted with 1 to 4 substituents independently selected from halo, cyano, hydroxy, oxo, $(C_1-C_6)$alkyl, $(C_1-C_6)$alkoxy, $(C_1-C_6)$alkoxy$(C_1-C_6)$alkyl, halo$(C_1-C_6)$alkyl, halo$(C_1-C_6)$alkoxy, $NH(C_1-C_6)$alkyl, $N((C_1-C_6)$alkyl$)_2$, $C(O)NH(C_1-C_6)$alkyl, $C(O)N((C_1-C_6)$alkyl$)_2$, $NHC(O)(C_1-C_6)$alkyl, $N(C_1-C_6)$alkyl$)C(O)(C_1-C_6)$alkyl), $C(O)(C_1-C_6)$alkyl, $C(O)O(C_1-C_6)$alkyl, $CO_2H$, $CONH_2$, $SO_2NH(C_1-C_6)$alkyl, and $SO_2N((C_1-C_6)$alkyl$)_2$.

2. The compound according claim 1, wherein m is 1 or 2.

3. The compound according claim 1, wherein each other $R^1$ is independently selected from fluoro, cyano, methyl, methoxy, and methoxymethyl.

4. The compound according claim 1, wherein $L^1$ is selected from a covalent bond, methylene, and ethylene.

5. The compound according claim 1, wherein $L^2$ is selected from a covalent bond, an oxygen atom, methylene, $OCH_2$, and $NHC(O)$.

6. The compound according claim 1, wherein group 'A' is selected from indanyl, phenyl, tetrahydrofuranyl, tetrahydropyranyl, tetralinyl, benzothiazolyl, imidazolyl, isoxazolyl, piperidinyl, pyrazolyl, pyridyl, pyrimidinyl, thiazolyl, 1,2,4-triazolyl, and quinolinyl.

7. The compound according claim 1, wherein group 'B' is selected from phenyl, oxazolyl, piperazinyl, piperidinyl, pyrazolyl, pyridyl, pyrimidinyl, pyrrolidinyl, 1,2-thiazolidinyl, and thiazolyl.

8. The compound according claim 1, wherein each carbocyclic and heterocyclic ring may be optionally substituted with 1 to 2 substituents independently selected from halo, cyano, hydroxy, oxo, $(C_1-C_6)$alkyl, $(C_1-C_6)$alkoxy, $CF_3$, $OCF_3$, and $NHC(O)(C_1-C_6)$alkyl.

9. The compound according to claim 1, wherein each carbocyclic and heterocyclic ring may be optionally substituted with 1 to 2 substituents independently selected from chloro, fluoro, cyano, hydroxy, oxo, methyl, isopropyl, methoxy, $CF_3$, $OCF_3$, $NHC(O)$isobutyl.

10. The compound according to claim 1, a tautomer thereof, or a pharmaceutically acceptable salt of said compound or tautomer, wherein:
m is 1;
$L^1$ is selected from a covalent bond, methylene, and ethylene;
$L^2$ is a covalent bond;
group 'A' is phenyl; group 'B' is pyridyl; and
each phenyl and pyridyl ring may be optionally substituted with 1 to 2 substituents independently selected from chloro, fluoro, cyano, hydroxy, methyl, isopropyl, methoxy, $CF_3$, $OCF_3$, NHC(O)isobutyl.

11. The compound according to claim 1, a tautomer thereof, or a pharmaceutically acceptable salt of said compound or tautomer, wherein:

n is 1; and group 'B' is a substituted 3 to 10-membered heterocyclic ring comprising 1 to 4 heteroatoms independently selected from N, O, and S.

12. A compound, wherein said compound is:

(3aR,6aR)-1-((4-(pyridin-3-yl)phenyl)sulfonyl)hexahydropyrrolo[3,4-b]pyrrole-5(1H)-carbonitrile, or a tautomer thereof, or a pharmaceutically acceptable salt of said compound or tautomer.

13. A pharmaceutical composition, comprising the compound according to claim 1, or a pharmaceutically acceptable salt of said compound or tautomer, together with a pharmaceutically acceptable diluent or carrier.

14. A pharmaceutical composition, comprising the compound according to claim 12, or a pharmaceutically acceptable salt of said compound or tautomer, together with a pharmaceutically acceptable diluent or carrier.

\* \* \* \* \*